US012321850B2

(12) United States Patent
Shin et al.

(10) Patent No.: US 12,321,850 B2
(45) Date of Patent: Jun. 3, 2025

(54) METHOD AND APPARATUS FOR CONTROLLING MASSAGE CHAIR

(71) Applicant: LG Electronics Inc., Seoul (KR)

(72) Inventors: Won Ho Shin, Seoul (KR); Beom Oh Kim, Gyeonggi-do (KR); Ji Chan Maeng, Seoul (KR); Tae Hyun Kim, Seoul (KR); Jong Hoon Chae, Seoul (KR)

(73) Assignee: LG Electronics Inc., Seoul (KR)

( * ) Notice: Subject to any disclaimer, the term of this patent is extended or adjusted under 35 U.S.C. 154(b) by 1413 days.

(21) Appl. No.: 16/733,474

(22) Filed: Jan. 3, 2020

(65) Prior Publication Data

US 2021/0110257 A1     Apr. 15, 2021

(30) Foreign Application Priority Data

Oct. 14, 2019   (KR) .................. 10-2019-0126844

(51) Int. Cl.
| | |
|---|---|
| G06N 3/08 | (2023.01) |
| A61F 7/00 | (2006.01) |
| A61H 7/00 | (2006.01) |
| A61H 15/00 | (2006.01) |
| A61H 23/02 | (2006.01) |
| G06N 20/00 | (2019.01) |
| G10L 15/22 | (2006.01) |

(52) U.S. Cl.
CPC .............. *G06N 3/08* (2013.01); *A61F 7/007* (2013.01); *A61H 15/0078* (2013.01); *A61H 7/004* (2013.01); *A61H 7/007* (2013.01); *A61H 23/02* (2013.01); *A61H 2201/0149* (2013.01); *A61H 2201/5043* (2013.01); *G06N 20/00* (2019.01); *G06T 2207/20084* (2013.01); *G10L 2015/223* (2013.01)

(58) Field of Classification Search
None
See application file for complete search history.

(56) References Cited

U.S. PATENT DOCUMENTS

| | | | | |
|---|---|---|---|---|
| 6,123,661 A | * | 9/2000 | Fukushima | ........... A61M 21/00 |
| | | | | 600/26 |
| 2018/0133101 A1 | * | 5/2018 | Inada | ...................... A61H 23/02 |
| 2019/0368179 A1 | * | 12/2019 | Tiagai | ...................... G06T 7/77 |

FOREIGN PATENT DOCUMENTS

| | | | | |
|---|---|---|---|---|
| KR | 10-2015-0135850 | | 12/2015 | |
| KR | 20160148899 | * | 12/2016 | ............. A47C 9/002 |
| KR | 10-1724643 | | 4/2017 | |
| KR | 10-2019-0084914 A | | 7/2019 | |
| KR | 10-2019-0089125 A | | 7/2019 | |

OTHER PUBLICATIONS

Jeong, Seung Ho, Machine Translation of KR 2016/0148899, Jun. 22, 2022 (Year: 2022).*
Office Action in Korean Appln. No. 10-2019-0126844, mailed on Jul. 24, 2024, 17 pages (with English translation).

* cited by examiner

*Primary Examiner* — Sean Shechtman
(74) *Attorney, Agent, or Firm* — Fish & Richardson P.C.

(57) ABSTRACT

A method and apparatus for controlling a massage chair have been disclosed. The method for controlling a massage chair comprises extracting multimedia information, detecting an action item, and controlling an action item. According to the present disclosure, the timing of the multimedia effect and the timing of the action item may be synchronized based on analysis using a deep neural network model through a 5G network.

20 Claims, 12 Drawing Sheets

METHOD AND APPARATUS FOR CONTROLLING MASSAGE CHAIR

CROSS-REFERENCE TO RELATED APPLICATION

This application claims benefit of priority to Korean Patent Application No. 10-2019-0126844, filed on Oct. 14, 2019, the entire disclosure of which is incorporated herein by reference.

BACKGROUND

1. Technical Field

The present disclosure relates to a massage chair control method and a control apparatus therefor, and more particularly, to a massage chair control method and a control apparatus therefor which are controlled to be linked with contents in an image to express effects used in the contents.

2. Description of Related Art

Massage chairs massage a user by using a special mechanism to relax stiff muscles or relieve fatigue and stress. General massage chairs are configured so that massage rollers or massage protrusions are arranged in positions corresponding to, for example, the neck, arms, back, waist, bottom, and legs of the user, and the massage rollers or massage protrusions are controlled according to operation of a motor so as to massage to the user.

Furthermore, massage chairs may be configured as a general type but also as a sitting mat type so as to be movable, or may be configured as a car seat in which a massage mechanism is embedded.

Recently, as virtual reality (VR)-related services become developed and propagated, a technology which combines the usage of VR contents by linking electronic devices and vehicles with VR is being actively researched.

As one related art, a method for controlling a massage chair based on a virtual reality image is disclosed. According to this related art, massage control information corresponding to the virtual reality image is transmitted to the massage chair, and a massage is provided to a user through the virtual reality image and the massage chair. However, according to this related art, when the massage control information is not found, a specific method for generating the massage control information is not disclosed. That is, the related art does not disclose how to determine a mood corresponding to the image by referring to background information, audio information, and object information, and which massage control information matches the determined mood.

Further, as another related art, a 4D experience system using IP-TV and a home massage chair is disclosed. According to this related art, 4D contents, in which massage chair driving data is added to 3D contents, are provided. However, the related art does not disclose how to determine driving data of the massage chair and only discloses that driving data of the massage chair, which is created in advance, is simply used.

SUMMARY OF THE INVENTION

An aspect of the present disclosure is to address an issue of the related art in that massage control information is determined only by a mood corresponding to image contents.

An aspect of the present disclosure is to address an issue of the related art in that massage control information is generated using an obscure algorithm.

An aspect of the present disclosure is to address an issue of the related art in that a control method is not disclosed when a massage chair and an apparatus for controlling the massage chair are provided through different routes.

An aspect of the present disclosure is to provide a massage chair control method which uses subtitles as well as images and sounds while addressing an issue of the related art in which the massage chair is controlled only by depending on images and sounds of image contents.

An aspect of the present disclosure is to provide a method for synchronizing the timing of playing content and controlling a massage chair by using a feedback signal while address an issue of the related art in which a method for synchronizing the timing of playing content and controlling the massage chair is not proposed.

While this disclosure includes specific embodiments, it will be apparent to one of ordinary skill in the art that various changes in form and details may be made in these embodiments without departing from the spirit and scope of claims and their equivalents. The embodiments described herein are to be considered in a descriptive sense only, and not for purposes of limitation. Further, it is understood that the objects and advantages of the present disclosure may be embodied by the means and a combination thereof in claims.

According to an aspect of the present disclosure, a massage chair control method includes: extracting multimedia information about a multimedia effect used in an input image through content analysis of the input image, detecting an action item of a massage chair which matches the multimedia effect, based on the multimedia information, and controlling the action item of the massage chair by using a control code of the action item.

Further, the content analysis of the input image is performed on at least one of a video signal, an audio signal, or a subtitle of the input image, and includes analysis of a frame of the input image before playing the input image at the time of real-time analysis of the input image.

Further, the content analysis of the input image is performed on a frame extracted from the input image using at least one of a deep neural network for video signal analysis, a deep neural network for audio signal analysis, or an algorithm for natural language processing of a subtitle.

Further, the content analysis of the input image includes classification of a multimedia effect used in the input image through video signal analysis, audio signal analysis, and natural language processing of a subtitle of the input image.

Further, the extracting of multimedia information includes extracting multimedia information based on the multimedia effect used in the input image and extracting information about a time in which the multimedia effect is used.

Further, the detecting of an action item includes matching the multimedia effect classified by a clustering model of a deep neural network and an action item of the massage chair which expresses the multimedia effect.

Further, the detecting of an action item includes matching an action item corresponding to at least one of, or a combination of, kneading, knocking, pressing, vibrating, rolling, rubbing, stretching, finger-pressure, zero-gravity reclining, or heating as an action item of the massage chair which matches the multimedia effect used for: an emotion including joy, anger, sorrow, pleasure, tension, and relief; a mood including fear, urgency, and mood change; and a situation including doing an action, being in space, being underwater, and flying.

Further, the controlling of an action item includes storing a control protocol of the massage chair, detecting a control code of the action item from the control protocol, and transmitting the control code to the massage chair.

Further, the controlling of an action item may be configured to include time synchronizing the action item, based on the feedback signal for the control code received from the massage chair and the time information included in the multimedia information.

Further, the massage chair control method may further include: sharing information with another user by directly or indirectly transmitting, through a server, at least one of information about the action item which matches the multimedia information, information about the control code of the massage chair which matches the action item, or the control protocol of the massage chair.

According to another aspect of the present disclosure, a massage chair control apparatus includes a processor configured to detect an action item of a massage chair which matches a multimedia effect based on multimedia information about the multimedia effect used in an input image through content analysis of the input image and a controller configured to control the action item of the massage chair using a control code of the action item.

Further, the processor may be configured to analyze contents of the input image with respect to at least one of a video signal, an audio signal, or a subtitle of the input image and analyze a frame of the input image before playing the input image at the time of real-time analysis of the input image.

Further, the processor may be configured to analyze the contents of the input image by using at least one of a deep neural network for video signal analysis, a deep neural network for audio signal analysis, or an algorithm for natural language processing of the subtitle, for the frame extracted from the input image.

Further, the processor may be configured to classify the multimedia effect used in the input image using a deep neural network trained by learning based on features of a video signal, an audio signal, and a subtitle of the input image.

Further, the processor may be configured to extract multimedia information based on the multimedia effect used in the input image and information about a time when the multimedia effect is used.

Further, the processor may be configured to match the multimedia effect classified by a clustering model of a deep neural network and an action item of the massage chair which expresses the multimedia effect.

Further, the processor may be configured to match an action item corresponding to at least one of, or a combination of, kneading, knocking, pressing, vibrating, rolling, rubbing, stretching, finger-pressure, zero-gravity reclining, or heating as an action item of the massage chair which matches the multimedia effect used for: an emotion including joy, anger, sorrow, pleasure, tension, and relief; a mood including fear, urgency, and mood change; and a special situation including doing an action, being in space, being underwater, and flying.

Further, the processor may be configured to detect a control code of the action item from the stored control protocol and the controller may be configured to control the transmission of the control code to the massage chair.

Further, the processor may be configured to adjust the controller to synchronize the timings of the multimedia effect and the action item based on the feedback signal for the control code received from the massage chair and the time information included in the multimedia information.

Further, the massage chair control apparatus may further include: a transceiver configured to share information with another user by directly or indirectly transmitting, through a server, at least one of information about the action item which matches the multimedia information, information about the control code which matches the action item, or the control protocol of the massage chair.

According to the present disclosure, it is possible to classify multimedia effects used in an input image, extract multimedia information, and extract action items, using a deep neural network model.

Further, it is possible to synchronize timings of a multimedia effect and a corresponding action item through a feedback signal from the massage chair.

Further, it is possible to control an action item of a massage chair linked with a multimedia effect of an input image.

BRIEF DESCRIPTION OF DRAWINGS

The above and other aspects, features, and advantages of the present disclosure will become apparent from the detailed description of the following aspects in conjunction with the accompanying drawings, in which.

DETAILED DESCRIPTION

Figure 1:
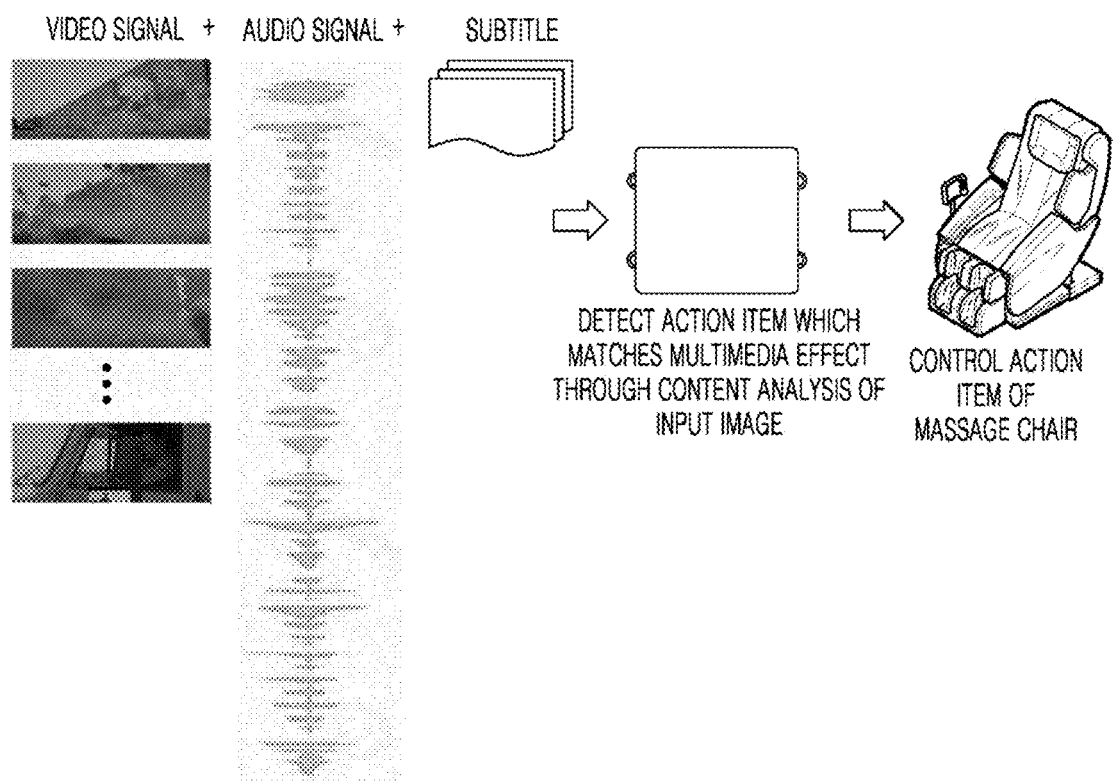
FIG. 1 is an exemplary diagram of a massage chair control method according to an embodiment of the present disclosure.

The embodiments disclosed in the present specification will be described in greater detail with reference to the accompanying drawings, and throughout the accompanying drawings, the same reference numerals are used to designate the same or similar components and redundant descriptions thereof are omitted. As used herein, the terms "module" and "unit" used to refer to components are used interchangeably in consideration of convenience of explanation, and thus, the terms per se should not be considered as having different meanings or functions. In addition, in the following description of the embodiments disclosed in this specification, the detailed description of related known technology will be omitted when it may obscure the subject matter of the embodiments according to the present disclosure. Further, the accompanying drawings are provided for more understanding of the embodiment disclosed in the present specification, but the technical spirit disclosed in the present invention is not limited by the accompanying drawings. It should be understood that all changes, equivalents, and alternatives included in the spirit and the technical scope of the present invention are included.

Although the terms first, second, third, and the like, may be used herein to describe various elements, components, regions, layers, and/or sections, these elements, components, regions, layers, and/or sections should not be limited by these terms. These terms are only used to distinguish one element from another.

Similarly, it will be understood that when an element is referred to as being "connected," "attached," or "coupled" to another element, it can be directly connected, attached, or coupled to the other element, or intervening elements may be present. In contrast, when an element is referred to as being "directly on," "directly engaged to," "directly connected to," or "directly coupled to" another element or layer, there may be no intervening elements or layers present.

4D movies are obtained by adding physical effects to 3D movies. For example, 4D movies screened in movie theaters are configured with a 4D chair and equipment for a 4D environment that correspond to 3D stereoscopic images. The physical effects used in the 4D movies are implemented while playing images, based on data for 4D effects included in 4D image data.

A method and apparatus for controlling a massage chair according to an embodiment of the present disclosure are distinguished from an apparatus or a method for realizing 4D movies in that the 4D effects are realized through a massage chair based on 2D or 3D images.

FIG. 1 is an exemplary diagram of a massage chair control method according to an embodiment of the present disclosure.

Referring to FIG. 1, a process of controlling an action item of a massage chair to match a multimedia effect through content analysis of an input image is schematically illustrated. The content analysis of the input image results in an analysis of video signals, audio signals, and subtitles which configure the image. The multimedia effect used in the image may be identified through content analysis, and a user may experience, as a tactile sensation, emotions, moods, and situations that an actor feels, by executing the action item of the massage chair in accordance with the multimedia effect.

The content analysis of the input image may include analysis of any one of, or a complex analysis of a combination of, a video signal, an audio signal, and a subtitle.

For example, analysis of a video signal may include analysis of a frame which configures an image. That is, an image frame may be extracted at random times, and the object may be analyzed from the image frame to analyze an image signal required to identify the multimedia effect.

When the analysis of a video signal is assumed to be a frame analysis, the audio signal may be analyzed based on the video signal analysis. For example, when a scene changes during the video signal analysis, an audio signal for a predetermined time may be analyzed at the time of change. The analysis of an audio signal may include analysis of various sounds, for example, sound effects and voices of characters.

That is, emotions of a character, moods in a scene, and scene development may be identified by analyzing a voice tone of the character.

In the case of a foreign movie, subtitle analysis may be included in the content analysis. Some of the emotions of a character, moods in a scene, and scene development may be identified through the subtitle analysis.

A control apparatus which performs the massage chair control method according to an embodiment of the present disclosure may correspond to an electronic apparatus that plays images. For example, a massage chair control apparatus according to an embodiment of the present disclosure may be implemented as a terminal 100 such as a smartphone or a set-top box which outputs a signal to a TV.

Figure 2:
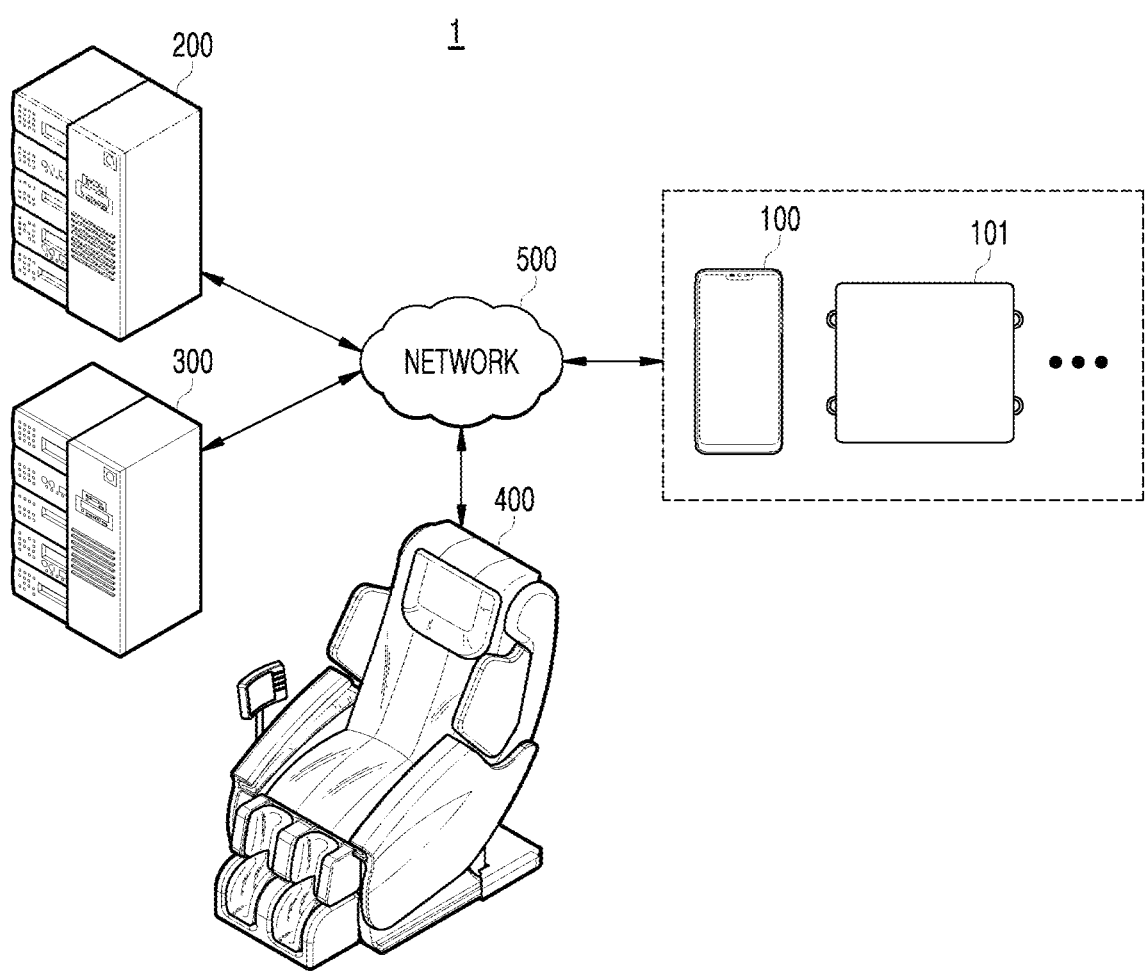
FIG. 2 is an exemplary diagram of a network environment to which a massage chair control apparatus according to an embodiment of the present disclosure is connected.

FIG. 2 is an exemplary diagram of a network environment to which a massage chair control apparatus according to an embodiment of the present disclosure is connected.

Referring to FIG. 2, as a massage chair control apparatus according to an embodiment of the present disclosure, a network environment 1, configured by the terminal 100, a set-top box 101, a learning device 200, a server 300, a massage chair 400, and a network 500, which connects the above components to mutually communicate is illustrated.

The massage chair control apparatus according to an embodiment of the present disclosure may be represented as a device such as various terminals 100 and the set-top box 101 depending on an implementation type but is not limited to the scope illustrated in FIG. 2.

Hereinafter, the massage chair control apparatus 100 according to an embodiment of the present disclosure will be described by focusing on the terminal 100 among various embodiments of the massage chair control apparatus. Unless other specific assumptions or conditions are described, the description of the terminal 100 may be applied to a different type of massage chair control apparatus such as a set-top box 101, as is.

The massage chair control apparatus 100 may control a massage chair by using the learning device 200. That is, the massage chair control apparatus 100 may use an artificial intelligence model, for example, a deep neural network, which is stored in the learning device 200, after being trained by the learning device 200. Further, the massage chair control apparatus 100 may download an artificial intelligence model trained by the learning device 200 and control the massage chair by using the artificial intelligence model. Details of the artificial intelligence will be described below.

The learning device 200 may train and evaluate the learning of an artificial intelligence model, for example, various deep neural network models, used for image content analysis according to an embodiment of the present disclosure. The artificial intelligence model, which is complete when the evaluating ends, may be stored in the learning device 200 or the massage chair control apparatus 100 to be used by the massage chair control apparatus 100. Details of the learning device 200 will be described below.

The network 500 may be an appropriate communication network including wired and wireless networks, such as a local area network (LAN), a wide area network (WAN), the Internet, the Intranet, and the extranet and a mobile network such as cellular, 3G LTE, 5G a Wi-Fi network, an AD hoc network, and a combination thereof.

The network 500 may include connection of network elements such as a hub, a bridge, a router, a switch, and a gateway. The network 500 may include one or more connected networks including a public network such as the Internet and a private network such as a secure corporate private network, for example, multiple network environments. Access to the network 500 may be provided via one or more wired or wireless access networks.

The massage chair control apparatus according to an embodiment of the present disclosure may be implemented as a set-top box which outputs an image signal to a TV. The network 500 may include data communication networks of various service providers for performing data communication through an IP, such as a communication network of an on-demand TV service provider, a communication network of a cable TV service provider, or a communication network of an Internet service provider.

The terminal 100 may transmit and receive data with the learning device 200 and the server 300 through a 5G network. Specifically, a voice-based action item proposing device 10 may perform data communication with the learning device 200 using at least one service of enhanced mobile broadband (eMBB), ultra-reliable and low latency communications (URLLC), or massive machine-type communications (mMTC) through the 5G network.

eMBB (enhanced mobile broadband) is a mobile broadband service, and multimedia contents, wireless data access, etc. are provided through eMBB (enhanced mobile broadband). Further, more improved mobile services such as a hotspot and a wideband coverage for receiving mobile traffic that are tremendously increasing can be provided through eMBB. Large traffic can be received to an area with little mobility and high density of users through a hotspot. A wide and stable wireless environment and user mobility can be secured by a wideband coverage.

A URLLC (ultra-reliable and low latency communications) service defines very severer requirements than existing LTE in terms of reliability in data transmission/reception and transmission delay, and 5G services for production process automation at industrial sites, telemedicine, telesurgery, transportation, safety, etc. are representative.

mMTC (massive machine-type communications) is a service that is not sensitive to transmission delay requiring a relatively small amount of data transmission. A large number of terminals more than common mobile phones such as sensors can simultaneously connect with a wireless access network by mMTC. In this case, the price of the communication module of a terminal should be low and a technology improved to increase power efficiency and save power is required to enable operation for several years without replacing or recharging a battery.

The artificial intelligence (AI) is one field of computer science and information technology that studies methods to make computers mimic intelligent human behaviors such as reasoning, learning, self-improving and the like.

In addition, the artificial intelligence does not exist on its own, but is rather directly or indirectly related to a number of other fields in computer science. In recent years, there have been numerous attempts to introduce an element of the artificial intelligence into various fields of information technology to solve problems in the respective fields.

Machine learning is an area of artificial intelligence that includes the field of study that gives computers the capability to learn without being explicitly programmed.

Specifically, the Machine Learning can be a technology for researching and constructing a system for learning, predicting, and improving its own performance based on empirical data and an algorithm for the same. The algorithms of the Machine Learning take a method of constructing a specific model in order to obtain the prediction or the determination based on the input data, rather than performing the strictly defined static program instructions.

Numerous machine learning algorithms have been developed for data classification in machine learning. Representative examples of such machine learning algorithms for data classification include a decision tree, a Bayesian network, a support vector machine (SVM), an artificial neural network (ANN), and so forth.

Decision tree refers to an analysis method that uses a tree-like graph or model of decision rules to perform classification and prediction.

Bayesian network may include a model that represents the probabilistic relationship (conditional independence) among a set of variables. Bayesian network may be appropriate for data mining via unsupervised learning.

SVM may include a supervised learning model for pattern detection and data analysis, heavily used in classification and regression analysis.

ANN is a data processing system modelled after the mechanism of biological neurons and interneuron connections, in which a number of neurons, referred to as nodes or processing elements, are interconnected in layers.

ANNs are models used in machine learning and may include statistical learning algorithms conceived from biological neural networks (particularly of the brain in the central nervous system of an animal) in machine learning and cognitive science.

ANNs may refer generally to models that have artificial neurons (nodes) forming a network through synaptic interconnections, and acquires problem-solving capability as the strengths of synaptic interconnections are adjusted throughout training.

The terms 'artificial neural network' and 'neural network' may be used interchangeably herein.

An ANN may include a number of layers, each including a number of neurons. In addition, the Artificial Neural Network can include the synapse for connecting between neuron and neuron.

An ANN may be defined by the following three factors: (1) a connection pattern between neurons on different layers; (2) a learning process that updates synaptic weights; and (3) an activation function generating an output value from a weighted sum of inputs received from a lower layer.

ANNs include, but are not limited to, network models such as a deep neural network (DNN), a recurrent neural network (RNN), a bidirectional recurrent deep neural network (BRDNN), a multilayer perception (MLP), and a convolutional neural network (CNN).

An ANN may be classified as a single-layer neural network or a multi-layer neural network, based on the number of layers therein.

A general Single-Layer Neural Network is composed of an input layer and an output layer.

In addition, a general Multi-Layer Neural Network is composed of an Input layer, one or more Hidden layers, and an Output layer.

The Input layer is a layer that accepts external data, the number of neurons in the Input layer is equal to the number of input variables, and the Hidden layer is disposed between the Input layer and the Output layer and receives a signal from the Input layer to extract the characteristics to transfer it to the Output layer. The Output layer receives a signal from the Hidden layer, and outputs an output value based on the received signal. The Input signal between neurons is multiplied by each connection strength (weight) and then summed, and if the sum is larger than the threshold of the neuron, the neuron is activated to output the output value obtained through the activation function.

A deep neural network with a plurality of hidden layers between the input layer and the output layer may be the most representative type of artificial neural network which enables deep learning, which is one machine learning technique.

The Artificial Neural Network can be trained by using training data. Herein, the training can mean a process of determining a parameter of the Artificial Neural Network by using training data in order to achieve the objects such as classification, regression, clustering, etc. of input data. As a representative example of the parameter of the Artificial Neural Network, there can be a weight given to a synapse or a bias applied to a neuron.

The Artificial Neural Network trained by the training data can classify or cluster the input data according to the pattern of the input data.

Meanwhile, the Artificial Neural Network trained by using the training data can be referred to as a trained model in the present specification.

Next, the learning method of the Artificial Neural Network will be described.

The learning method of the Artificial Neural Network can be largely classified into Supervised Learning, Unsupervised Learning, Semi-supervised Learning, and Reinforcement Learning.

The Supervised Learning is a method of the Machine Learning for inferring one function from the training data.

Then, among the thus inferred functions, outputting consecutive values is referred to as regression, and predicting and outputting a class of an input vector is referred to as classification.

In the Supervised Learning, the Artificial Neural Network is learned in a state where a label for the training data has been given.

Here, the label may refer to a target answer (or a result value) to be guessed by the artificial neural network when the training data is inputted to the artificial neural network.

Throughout the present specification, the target answer (or a result value) to be guessed by the artificial neural network when the training data is inputted may be referred to as a label or labeling data.

In addition, in the present specification, setting the label to the training data for training of the Artificial Neural Network is referred to as labeling the labeling data on the training data.

Training data and labels corresponding to the training data together may form a single training set, and as such, they may be inputted to an artificial neural network as a training set.

Meanwhile, the training data represents a plurality of features, and the labeling the label on the training data can mean that the feature represented by the training data is labeled. In this case, the training data can represent the feature of the input object in the form of a vector.

The Artificial Neural Network can infer a function of the relationship between the training data and the labeling data by using the training data and the labeling data. Then, the parameter of the Artificial Neural Network can be determined (optimized) by evaluating the function inferred from the Artificial Neural Network.

Unsupervised learning is a machine learning method that learns from training data that has not been given a label.

More specifically, unsupervised learning may be a training scheme that trains an artificial neural network to discover a pattern within given training data and perform classification by using the discovered pattern, rather than by using a correlation between given training data and labels corresponding to the given training data.

Examples of unsupervised learning include, but are not limited to, clustering and independent component analysis.

Examples of artificial neural networks using unsupervised learning include, but are not limited to, a generative adversarial network (GAN) and an autoencoder (AE).

GAN is a machine learning method in which two different artificial intelligences, a generator and a discriminator, improve performance through competing with each other.

The generator may be a model generating new data that generates new data based on true data.

The discriminator may be a model recognizing patterns in data that determines whether inputted data is from the true data or from the new data generated by the generator.

Furthermore, the generator may receive and learn from data that has failed to fool the discriminator, while the discriminator may receive and learn from data that has succeeded in fooling the discriminator. Accordingly, the generator may evolve so as to fool the discriminator as effectively as possible, while the discriminator evolves so as to distinguish, as effectively as possible, between the true data and the data generated by the generator.

An auto-encoder (AE) is a neural network which aims to reconstruct its input as output.

More specifically, AE may include an input layer, at least one hidden layer, and an output layer.

Since the number of nodes in the hidden layer is smaller than the number of nodes in the input layer, the dimensionality of data is reduced, thus leading to data compression or encoding.

Furthermore, the data outputted from the hidden layer may be inputted to the output layer. Given that the number of nodes in the output layer is greater than the number of nodes in the hidden layer, the dimensionality of the data increases, thus leading to data decompression or decoding.

Furthermore, in the AE, the inputted data is represented as hidden layer data as interneuron connection strengths are adjusted through training. The fact that when representing information, the hidden layer is able to reconstruct the inputted data as output by using fewer neurons than the input layer may indicate that the hidden layer has discovered a hidden pattern in the inputted data and is using the discovered hidden pattern to represent the information.

Semi-supervised learning is machine learning method that makes use of both labeled training data and unlabeled training data.

One semi-supervised learning technique involves reasoning the label of unlabeled training data, and then using this reasoned label for learning. This technique may be used advantageously when the cost associated with the labeling process is high.

Reinforcement learning may be based on a theory that given the condition under which a reinforcement learning agent can determine what action to choose at each time instance, the agent can find an optimal path to a solution solely based on experience without reference to data.

The Reinforcement Learning can be mainly performed by a Markov Decision Process (MDP).

Markov decision process consists of four stages: first, an agent is given a condition containing information required for performing a next action; second, how the agent behaves in the condition is defined; third, which actions the agent should choose to get rewards and which actions to choose to get penalties are defined; and fourth, the agent iterates until future reward is maximized, thereby deriving an optimal policy.

An artificial neural network is characterized by features of its model, the features including an activation function, a loss function or cost function, a learning algorithm, an optimization algorithm, and so forth. Also, the hyperparameters are set before learning, and model parameters can be set through learning to specify the architecture of the artificial neural network.

For instance, the structure of an artificial neural network may be determined by a number of factors, including the number of hidden layers, the number of hidden nodes included in each hidden layer, input feature vectors, target feature vectors, and so forth.

Hyperparameters may include various parameters which need to be initially set for learning, much like the initial values of model parameters. Also, the model parameters may include various parameters sought to be determined through learning.

For instance, the hyperparameters may include initial values of weights and biases between nodes, mini-batch size, iteration number, learning rate, and so forth. Furthermore, the model parameters may include a weight between nodes, a bias between nodes, and so forth.

Loss function may be used as an index (reference) in determining an optimal model parameter during the learning process of an artificial neural network. Learning in the artificial neural network involves a process of adjusting model parameters so as to reduce the loss function, and the purpose of learning may be to determine the model parameters that minimize the loss function.

Loss functions typically use means squared error (MSE) or cross entropy error (CEE), but the present disclosure is not limited thereto.

Cross-entropy error may be used when a true label is one-hot encoded. One-hot encoding may include an encoding method in which among given neurons, only those corresponding to a target answer are given 1 as a true label value, while those neurons that do not correspond to the target answer are given 0 as a true label value.

In machine learning or deep learning, learning optimization algorithms may be deployed to minimize a cost function, and examples of such learning optimization algorithms include gradient descent (GD), stochastic gradient descent (SGD), momentum, Nesterov accelerate gradient (NAG), Adagrad, AdaDelta, RMSProp, Adam, and Nadam.

GD includes a method that adjusts model parameters in a direction that decreases the output of a cost function by using a current slope of the cost function.

The direction in which the model parameters are to be adjusted may be referred to as a step direction, and a size by which the model parameters are to be adjusted may be referred to as a step size.

Here, the step size may mean a learning rate.

GD obtains a slope of the cost function through use of partial differential equations, using each of model parameters, and updates the model parameters by adjusting the model parameters by a learning rate in the direction of the slope.

SGD may include a method that separates the training dataset into mini batches, and by performing gradient descent for each of these mini batches, increases the frequency of gradient descent.

Adagrad, AdaDelta and RMSProp may include methods that increase optimization accuracy in SGD by adjusting the step size, and may also include methods that increase optimization accuracy in SGD by adjusting the momentum and step direction. Adam may include a method that combines momentum and RMSProp and increases optimization accuracy in SGD by adjusting the step size and step direction. Nadam may include a method that combines NAG and RMSProp and increases optimization accuracy by adjusting the step size and step direction.

Learning rate and accuracy of an artificial neural network rely not only on the structure and learning optimization algorithms of the artificial neural network but also on the hyperparameters thereof. Therefore, in order to obtain a good learning model, it is important to choose a proper structure and learning algorithms for the artificial neural network, but also to choose proper hyperparameters.

In general, the artificial neural network is first trained by experimentally setting hyperparameters to various values, and based on the results of training, the hyperparameters can be set to optimal values that provide a stable learning rate and accuracy.

The massage chair control apparatus 100 according to an embodiment of the present disclosure may use an artificial intelligence model trained by the learning device 200 or retrain the artificial intelligence model that was trained with a user's personal data with regard to the artificial intelligence required to perform an object recognizing function, a voice recognizing function, and natural language processing during the content analysis process using a video signal, an audio signal, and a subtitle.

Hereinafter, an embodiment of the present disclosure will be described with respect to the mobile terminal 100 and the set-top box 101 which represent the massage chair control apparatus according to the embodiment of the present disclosure. Further, unless other specific assumptions or conditions are provided, the description of the mobile terminal 100 and the set-top box 101 may be applied to another exemplary embodiment as it is.

Figure 3:
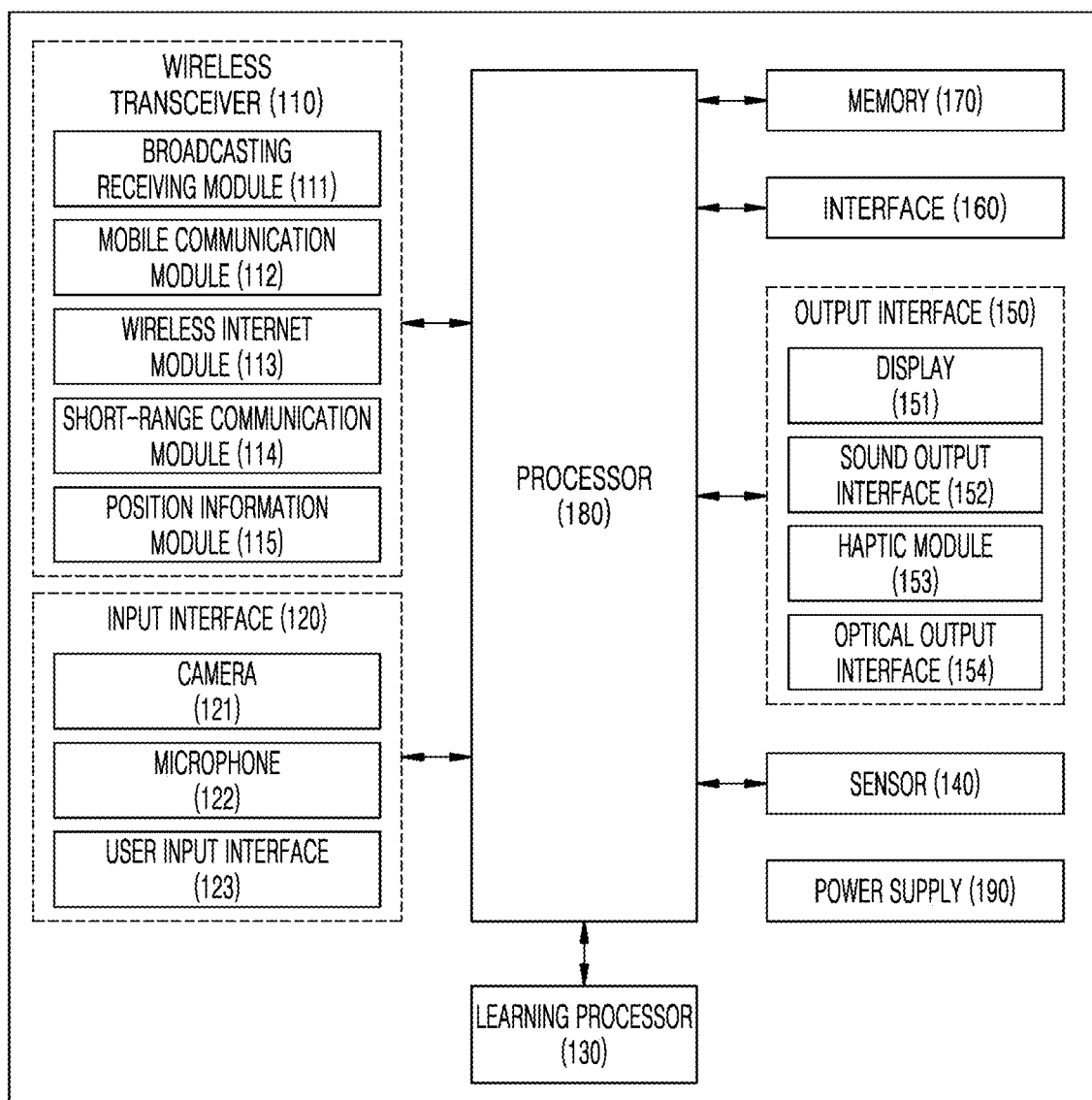
FIG. 3 is a block diagram of a terminal corresponding to an embodiment of a massage chair control apparatus.

FIG. 3 is a block diagram of a terminal corresponding to an embodiment of a massage chair control apparatus.

The terminal 100 may be implemented as a stationary terminal and a mobile terminal, such as a mobile phone, a projector, a mobile phone, a smartphone, a laptop computer, a terminal for digital broadcast, a personal digital assistant (PDA), a portable multimedia player (PMP), a navigation system, a slate PC, a tablet PC, an ultrabook, a wearable device (for example, a smartwatch, a smart glass, and a head mounted display (HMD)), a set-top box (STB), a digital multimedia broadcast (DMB) receiver, a radio, a laundry machine, a refrigerator, a desktop computer, a digital signage.

That is, the terminal 100 may be implemented as various home appliances used at home and also applied to a fixed or mobile robot.

The terminal 100 may perform a function of a voice agent. The voice agent may be a program which recognizes a voice of the user and outputs a response appropriate for the recognized voice of the user as a voice.

Referring to FIG. 3, the terminal 100 may include a wireless transceiver 110, an input interface 120, a learning processor 130, a sensor 130, an output interface 150, an interface 160, a memory 170, a processor 180, and a power supply 190.

A trained model may be loaded in the terminal 100.

The learning model may be implemented by hardware, software, or a combination of hardware and software. When a part or all of the learning model is implemented by software, one or more commands which configure the learning model may be stored in the memory 170.

The wireless transceiver 110 may include at least one of a broadcasting receiving module 111, a mobile communication module 112, a wireless internet module 113, a short-range communication module 114, or a position information module 115.

The broadcasting receiving module 111 receives broadcast signals and/or broadcast-related information through a broadcast channel from an external broadcast management server.

The mobile communication module 112 may transmit/receive a wireless signal to/from at least one of a base station, an external terminal, or a server on a mobile communication network established according to the technical standards or communication methods for mobile communication (for example, Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), and Long Term Evolution-Advanced (LTE-A)).

The wireless internet module 113 refers to a module for wireless internet access and may be built in or external to the terminal 100. The wireless internet module 113 may be configured to transmit/receive a wireless signal in a communication network according to wireless internet technologies.

The wireless internet technologies may include Wireless LAN (WLAN), Wireless-Fidelity (Wi-Fi), Wi-Fi Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A).

The short-range communication module 114 may support Short-range communication by using at least one of Bluetooth™, Radio Frequency Identification (RFID), Infrared Data Association (IrDA), Ultra Wideband (UWB), ZigBee, Near Field Communication (NFC), Wireless-Fidelity (Wi-Fi), Wi-Fi Direct, or Wireless Universal Serial Bus (USB) technologies.

The location information module 115 is a module for obtaining the location (or the current location) of a mobile terminal, and its representative examples include a global positioning system (GPS) module or a Wi-Fi module. For example, the mobile terminal may obtain its position by using a signal transmitted from a GPS satellite through the GPS module.

The input interface 120 may include a camera 121 which inputs an image signal, a microphone 122 which receives an audio signal, and a user input interface 123 which receives information from the user.

Voice data or image data collected by the input interface 120 is analyzed to be processed as a control command of the user.

The input interface 120 may obtain training data for training a model and input data used to obtain an output using the trained model.

The input interface 120 may obtain input data which is not processed, and, in this case, the processor 180 or the learning processor 130 pre-processes the obtained data to generate training data to be input to the model learning or pre-processed input data.

Here, the preprocessing of input data may refer to extracting an input feature from the input data.

The input interface 120 is provided to input image information (or signal), audio information (or signal), data, or information input from the user and in order to input the image information, the terminal 100 may include one or a plurality of cameras 121.

The camera 121 processes an image frame such as a still image or a moving image obtained by an image sensor in a video call mode or a photographing mode. The processed image frame may be displayed on the display 151 or stored in the memory 170.

The microphone 122 processes an external sound signal as electrical voice data. The processed voice data may be utilized in various forms in accordance with a function which is being performed by the terminal 100 (or an application program which is being executed). In the microphone 122, various noise removal algorithms which remove a noise generated during the process of receiving the external sound signal may be implemented.

The user input interface 123 receives information from the user and when the information is input through the user input interface 123, the processor 180 may control the operation of the terminal 100 so as to correspond to the input information.

The user input interface 123 may include a mechanical input interface (or a mechanical key, for example, a button located on a front, rear, or side surface of the terminal 100, a dome switch, a jog wheel, or a jog switch) and a touch type input interface. For example, the touch type input interface may be formed by a virtual key, a soft key, or a visual key which is disposed on the touch screen through a software process or a touch key which is disposed on a portion other than the touch screen.

The learning processor 130 learns the model configured by an artificial neural network using the training data.

Specifically, the learning processor 130 repeatedly trains the artificial neural network using the aforementioned various learning techniques to determine optimized model parameters of the artificial neural network.

In this specification, the artificial neural network which is trained using training data to determine parameters may be referred to as a learning model or a trained model.

In this case, the learning model may be used to deduce a result for the new input data, rather than the training data.

The learning processor 130 may be configured to receive, classify, store, and output information to be used for data mining, data analysis, intelligent decision making, and machine learning algorithm and techniques.

The learning processor 130 may include one or more memory units configured to store data which is received, detected, sensed, generated, previously defined, or output by another component, device, the terminal, or a device which communicates with the terminal.

The learning processor 130 may include a memory which is combined with or implemented in the terminal. In some exemplary embodiments, the learning processor 130 may be implemented using the memory 170.

Selectively or additionally, the learning processor 130 may be implemented using a memory related to the terminal, such as an external memory which is directly coupled to the terminal or a memory maintained in the server which communicates with the terminal.

According to another exemplary embodiment, the learning processor 130 may be implemented using a memory maintained in a cloud computing environment or other remote memory locations accessible by the terminal via a communication method such as a network.

The learning processor 130 may be configured to store data in one or more databases to identify, index, categorize, manipulate, store, search, and output data in order to be used for supervised or non-supervised learning, data mining, predictive analysis, or used in the other machine. Here, the database may be implemented using the memory 170, a memory 230 of the learning device 200, a memory maintained in a cloud computing environment or other remote memory locations accessible by the terminal via a communication method such as a network.

Information stored in the learning processor 130 may be used by the processor 180 or one or more controllers of the terminal using an arbitrary one of different types of data analysis algorithms and machine learning algorithms.

As an example of such an algorithm, a k-nearest neighbor system, fuzzy logic (for example, possibility theory), a neural network, a Boltzmann machine, vector quantization, a pulse neural network, a support vector machine, a maximum margin classifier, hill climbing, an inductive logic system, a Bayesian network, (for example, a finite state machine, a Mealy machine, a Moore finite state machine), a classifier tree (for example, a perceptron tree, a support vector tree, a Markov Tree, a decision tree forest, an arbitrary forest), a reading model and system, artificial fusion, sensor fusion, image fusion, reinforcement learning, augmented reality, pattern recognition, automated planning, and the like, may be provided.

The processor 180 may determine or predict at least one executable operation of the terminal based on information which is determined or generated using the data analysis and the machine learning algorithm. To this end, the processor 180 may request, search, receive, or utilize the data of the learning processor 130 and control the terminal to execute a predicted operation or a desired operation among the at least one executable operation.

The processor 180 may perform various functions which implement intelligent emulation (that is, a knowledge based system, an inference system, and a knowledge acquisition system). This may be applied to various types of systems (for example, a fuzzy logic system) including an adaptive system, a machine learning system, and an artificial neural network.

The processor 180 may include sub modules which enable operations involving voice and natural language voice processing, such as an I/O processing module, an environmental condition module, a speech to text (STT) processing module, a natural language processing module, a workflow processing module, and a service processing module.

The sub modules may have an access to one or more systems or data and a model, or a subset or a super set those of in the terminal. Further, each of the sub modules may provide various functions including a glossarial index, user data, a workflow model, a service model, and an automatic speech recognition (ASR) system.

According to another exemplary embodiment, another aspect of the processor 180 or the terminal may be implemented by the above-described sub module, a system, data, and a model.

In some exemplary embodiments, based on the data of the learning processor 130, the processor 180 may be configured to detect and sense requirements based on contextual conditions expressed by user input or natural language input or user's intention.

The processor 180 may actively derive and obtain information required to completely determine the requirement based on the contextual conditions or the user's intention. For example, the processor 180 may actively derive information required to determine the requirements, by analyzing past data including historical input and output, pattern matching, unambiguous words, and input intention.

The processor 180 may determine a task flow to execute a function responsive to the requirements based on the contextual condition or the user's intention.

The processor 180 may be configured to collect, sense, extract, detect and/or receive a signal or data which is used for data analysis and a machine learning task through one or more sensing components in the terminal, to collect information for processing and storing in the learning processor 130.

The information collection may include sensing information by a sensor, extracting of information stored in the memory 170, or receiving information from other equipment, an entity, or an external storage device through a transceiver.

The processor 180 collects usage history information from the terminal and stores the information in the memory 170.

The processor 180 may determine best matching to execute a specific function using stored usage history information and predictive modeling.

The processor 180 may receive or sense surrounding environment information or other information through the sensor 140.

The processor 180 may receive a broadcasting signal and/or broadcasting related information, a wireless signal, or wireless data through the wireless transceiver 110.

The processor 180 may receive image information (or a corresponding signal), audio information (or a corresponding signal), data, or user input information from the input interface 120.

The processor 180 may collect the information in real time, process or classify the information (for example, a knowledge graph, a command policy, a personalized database, or a conversation engine) and store the processed information in the memory 170 or the learning processor 130.

When the operation of the terminal is determined based on data analysis and a machine learning algorithm and technology, the processor 180 may control the components of the terminal to execute the determined operation. Further, the processor 180 may control the terminal in accordance with the control command to perform the determined operation.

When a specific operation is performed, the processor 180 analyzes history information indicating execution of the specific operation through the data analysis and the machine learning algorithm and technology and updates the information which is previously learned based on the analyzed information.

Therefore, the processor 180 may improve precision of a future performance of the data analysis and the machine learning algorithm and technology based on the updated information, together with the learning processor 130.

The sensor 140 may include one or more sensors which sense at least one of information in the mobile terminal, surrounding environment information around the mobile terminal, or user information.

For example, the sensor 140 may include at least one of a proximity sensor, an illumination sensor, a touch sensor, an acceleration sensor, a magnetic sensor, a G-sensor, a gyroscope sensor, a motion sensor, an RGB sensor, an infrared (IR) sensor, a finger scan sensor, an ultrasonic sensor, an optical sensor (for example, a camera 121), a microphone 122, a battery gauge, an environment sensor (for example, a barometer, a hygrometer, a thermometer, a radiation sensor, a thermal sensor, or a gas sensor), or a chemical sensor (for example, an electronic nose, a healthcare sensor, or a biometric sensor). On the other hand, the terminal 100 disclosed in the present disclosure may combine various kinds of information sensed by at least two of the above-mentioned sensors and may use the combined information.

The output interface 150 is intended to generate an output related to a visual, aural, or tactile stimulus and may include at least one of a display 151, sound output interface 152, haptic module 153, or optical output interface 154.

The display 151 displays (outputs) information processed in the terminal 100. For example, the display 151 may display execution screen information of an application program driven in the terminal 100 and user interface (UI) and graphic user interface (GUI) information in accordance with the execution screen information.

The display 151 forms a mutual layered structure with a touch sensor or is formed integrally to be implemented as a touch screen. The touch screen may simultaneously serve as a user input interface 123 which provides an input interface between the terminal 100 and the user and provide an output interface between the terminal 100 and the user.

The sound output interface 152 may output audio data received from the wireless transceiver 110 or stored in the memory 170 in a call signal reception mode, a phone-call mode, a recording mode, a voice recognition mode, or a broadcasting reception mode.

The sound output interface 152 may include at least one of a receiver, a speaker, or a buzzer.

The haptic module 153 may generate various tactile effects that the user may feel. A representative example of the tactile effect generated by the haptic module 153 may be vibration.

The optical output interface 154 outputs a signal for notifying occurrence of an event using light of a light source of the terminal 100. Examples of the event generated in the terminal 100 may be message reception, call signal reception, missed call, alarm, schedule notification, email reception, and information reception through an application.

The interface 160 serves as a passage with various types of external devices which are connected to the terminal 100. The interface 160 may include at least one of a wired/wireless headset port, an external charger port, a wired/wireless data port, a memory card port, a port which connects a device equipped with an identification module, an audio input/output (I/O) port, a video input/output (I/O) port, or an earphone port. The terminal 100 may perform appropriate control related to the connected external device in accordance with the connection of the external device to the interface 160.

The identification module is a chip in which various information for authenticating a usage right of the terminal 100 is stored and includes a user identification module (UIM), a subscriber identify module (SIM), and a universal subscriber identity module (USIM). The device with an identification module (hereinafter, "identification device") may be manufactured as a smart card. Therefore, the identification device may be connected to the terminal 100 through the interface 160.

The memory 170 stores data which supports various functions of the terminal 100.

The memory 170 may store various application programs (or applications) driven in the terminal 100, data for the operation of the terminal 100, commands, and data (for example, at least one algorithm information for machine learning) for the operation of the learning processor 130.

The memory 170 may store the model which is learned in the learning processor 130 or the learning device 200.

If necessary, the memory 170 may store the trained model by dividing the model into a plurality of versions depending on a training timing or a training progress.

In this case, the memory 170 may store input data obtained from the input interface 120, learning data (or training data) used for model learning, a learning history of the model, and so forth.

In this case, the input data stored in the memory 170 may be not only data which is processed to be suitable for the model learning but also input data itself which is not processed.

In addition to the operation related to the application program, the processor 180 may generally control an overall operation of the terminal 100. The processor 180 may process a signal, data, or information which is input or output through the above-described components or drives the application programs stored in the memory 170 to provide or process appropriate information or functions to the user.

Further, in order to drive the application program stored in the memory 170, the processor 180 may control at least some of components described with reference to FIG. 3. Moreover, the processor 180 may combine and operate at least two of components included in the terminal 100 to drive the application program.

As described above, the processor 180 may control an operation related to the application program and an overall operation of the terminal 100. For example, when the state of the terminal satisfies a predetermined condition, the processor 180 may execute or release a locking state which restricts an input of a control command of a user for the applications.

The power supply 190 is applied with external power or internal power to supply the power to the components included in the terminal 100 under the control of the processor 180. The power supply 190 includes a battery and the battery may be an embedded battery or a replaceable battery.

Figure 4:
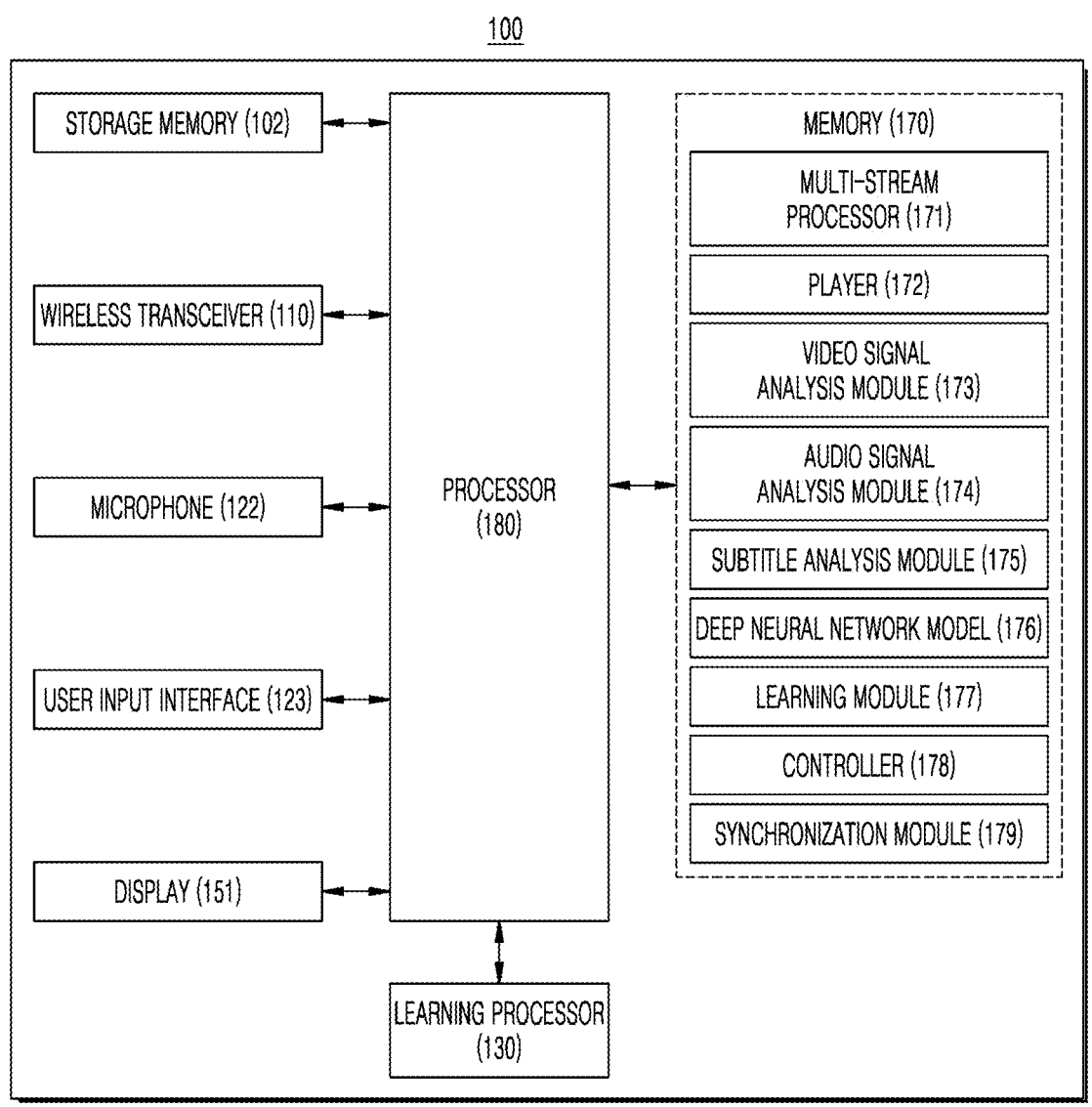
FIG. 4 is a block diagram of a memory of FIG. 3.

FIG. 4 is a block diagram of a memory of FIG. 3.

Figure 5:
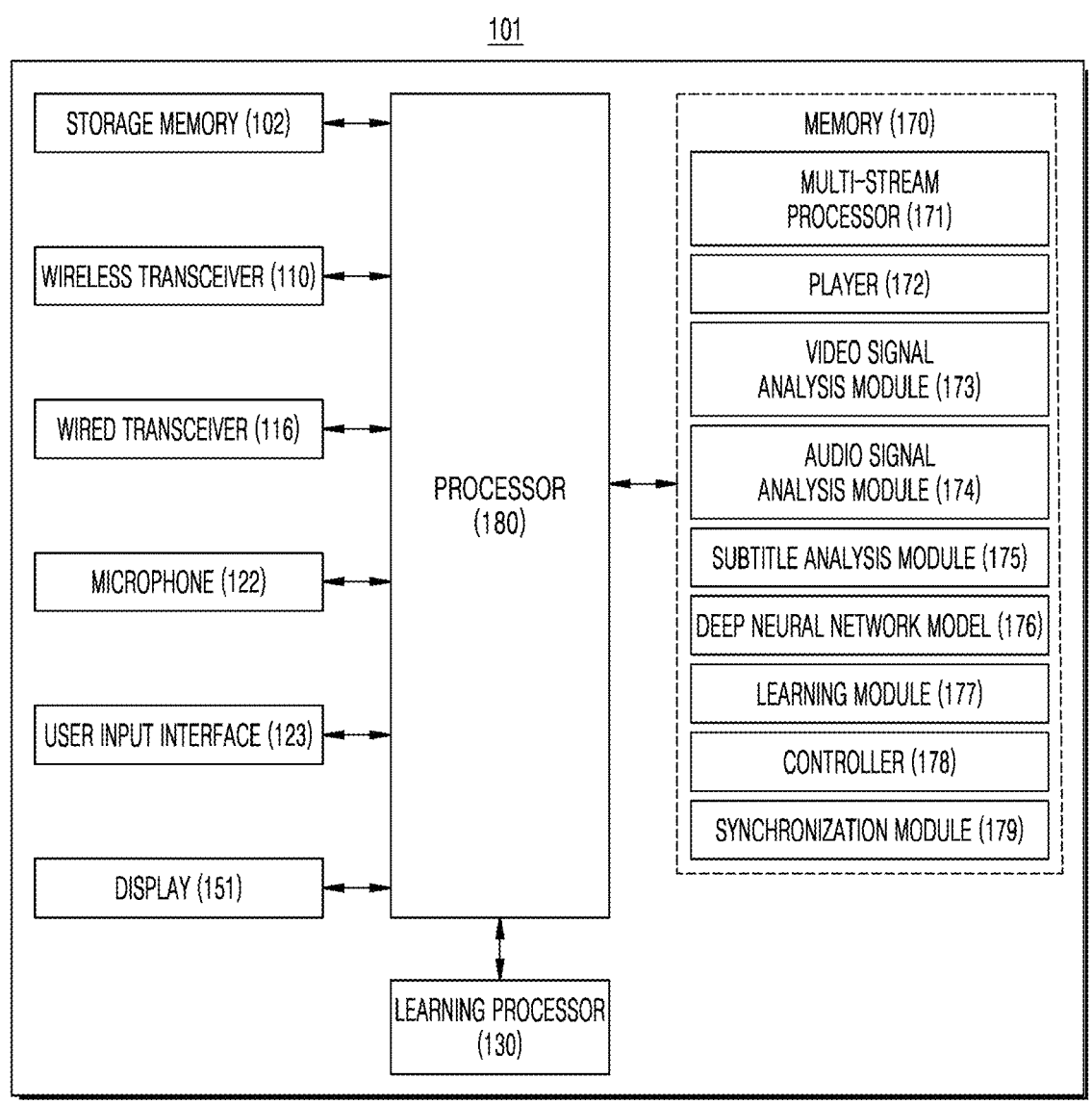
FIG. 5 is a block diagram of a set-top box corresponding to an embodiment of a massage chair control apparatus.

FIG. 5 is a block diagram of a set-top box corresponding to an embodiment of a massage chair.

The massage chair control apparatus according to an embodiment of the present disclosure may be implemented as the terminal 100 or the set-top box 101. Compared with the terminal 100, which is connected only to a wireless network 500, the set-top box 101 may be configured to include a wireless transceiver and a wired transceiver to be connected to wireless and wired networks 500, respectively.

Referring to FIGS. 4 and 5, a software module, stored in a memory 170 included in the terminal 100 and the set-top box 101, that serves as a massage chair control apparatus is illustrated. In the scope of an application module loaded in the memory 170, in addition to an operating system and a system application which manages hardware, a multi-stream processor 171, a player 172, a video signal analysis module 173, an audio signal analysis module 174, a subtitle analysis module 175, a deep neural network model 176, a learning module 177, a controller 178, and a synchronization module 179 may be included as applied applications. The memory 170 and at least one applied applications may be implemented by at least one hardware such as an application specific integrated circuit.

The multi-stream processor 171 may process at least one of UDP uni/multicast, a local/network file, or standard real time streaming protocol (RTSP)/real time transport protocol (RTP).

The player 172 plays local/network files and various streaming data processed by the multi-stream processor 171. The player 172 may include a demultiplexer, a decoder, and an A/V out. The demultiplexer separates video and audio from file data or streaming data.

The decoder decodes a video codec and decodes video and audio data using the video codec. The decoder includes a video codec and an audio codec. Here, 4 k×2 kp60, H.265, 4 kp60, 1080p60 H.264/MPEG2, MVC 3D Stereo L4.1, VP8 1080p60, and VC1 1080i60 may be included as the video codec. AC3/AC3Plus, AAC/AACPlus, MPEG1 Audio (mp3), WMA/WMAPro, WAV, Vorbis, and Flac may be included as the audio codec. However, the codec may be upgraded through the server 300, together with the firmware upgrade.

The decoded video and audio signals may be output through the A/V out. The video and audio signals may be transmitted to a TV, a projector, or an audio processor through a dedicated cable. A high definition multimedia interface (HDMI) cable, which is an example of the dedicated cable, may transmit a compressed or uncompressed image signal, voice signal, and control signal through one cable.

An image content analysis function based on the video signal, which is related to the video signal analysis module 173, may be performed by various operation functions of the processor 180.

An image content analysis function based on the audio signal, which is related to the audio signal analysis module 174, may be performed by various operation functions of the processor 180.

An image content analysis function based on the subtitles, which is related to the subtitle analysis module 175, may be performed by various operation functions of the processor 180.

The deep neural network model 176 may analyze contents by using at least one of the video signal, the audio signal, or the subtitle. For example, a deep learning-based CNN may recognize an object in the image by video signal analysis and extract multimedia information about an image effect based on object recognition. Further, a deep learning-based RNN may extract multimedia information about a sound effect by the audio signal analysis. Further, an algorithm and an artificial intelligence model for processing various natural languages may perform the natural language processing on dialogues of characters in the image based on the subtitle.

A function of training the already trained artificial intelligence model by using personal data of the user, which is related to the learning model 177, for example, a deep neural network, may be performed by various operating functions of the processor 180 or the learning processor 130.

The controller 178 outputs a control code required to execute an action item of the massage chair. The output control code is transmitted to the massage chair, through an infrared ray or a wireless LAN, in accordance with a communication method.

The synchronization module 179 synchronizes the transmission of the control code by the massage chair control apparatus 100 with an action item of the massage chair executed by the control code.

Figure 6:
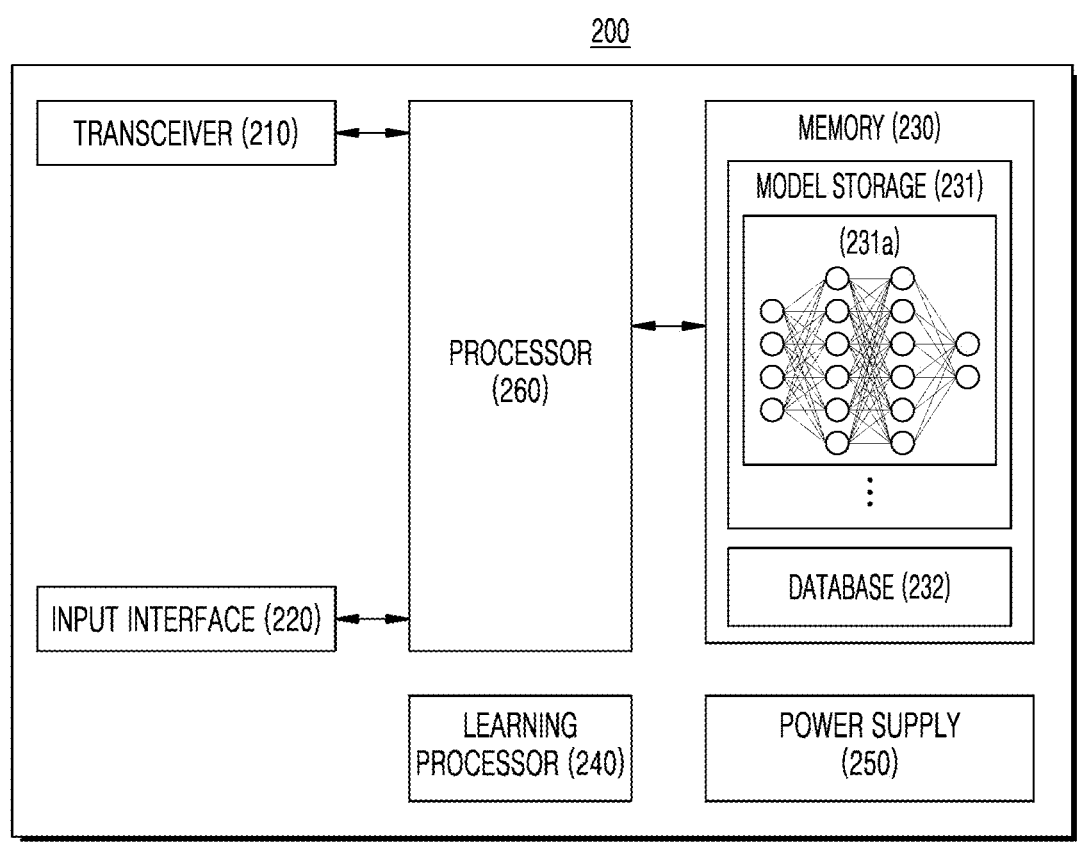
FIG. 6 is a block diagram of a learning device according to an embodiment of the present disclosure.

FIG. 6 is a block diagram of a learning device according to an embodiment of the present disclosure.

The learning device 200 is a device or a server which is separately configured at the outside of the terminal 100 and may perform the same function as the learning processor 130 of the terminal 100.

That is, the learning device 200 may be configured to receive, classify, store, and output information to be used for data mining, data analysis, intelligent decision making, and machine learning algorithms. Here, the machine learning algorithm may include a deep learning algorithm.

The learning device 200 may communicate with at least one terminal 100 and derive a result by analyzing or learning the data on behalf of the terminal 100. Here, the meaning of "on behalf of the other device" may be distribution of a computing power by means of distributed processing.

The learning device 200 of the artificial neural network is various devices for learning an artificial neural network and normally, refers to a server, and also referred to as a learning device or a learning server.

Specifically, the learning device 200 may be implemented not only by a single server, but also by a plurality of server sets, a cloud server, or a combination thereof.

That is, the learning device 200 is configured as a plurality of learning devices to configure a learning device set (or a cloud server) and at least one learning device 200 included in the learning device set may derive a result by analyzing or learning the data through the distributed processing.

The learning device 200 may transmit a model trained by the machine learning or the deep learning to the terminal 100 periodically or upon the request.

Referring to FIG. 6, the learning device 200 may include a transceiver 210, an input interface 220, a memory 230, a learning processor 240, a power supply 250, a processor 260, and so forth.

The transceiver 210 may correspond to a configuration including the wireless transceiver 110 and the interface 160 of FIG. 3. That is, the transceiver may transmit and receive data with the other device through wired/wireless communication or an interface.

The input interface 220 is a configuration corresponding to the input interface 120 of FIG. 3 and may receive the data through the transceiver 210 to obtain data.

The input interface 220 may obtain input data for acquiring an output using training data for model learning and a trained model.

The input interface 220 may obtain input data which is not processed, and, in this case, the processor 260 may pre-process the obtained data to generate training data to be input to the model learning or pre-processed input data.

In this case, the pre-processing on the input data performed by the input interface 220 may refer to extracting of an input feature from the input data.

The memory 230 is a configuration corresponding to the memory 170 of FIG. 3.

The memory 230 may include a model storage 231, a database 232, and so forth.

The model storage 231 stores a model (or an artificial neural network 231a) which is learning or trained through the learning processor 240 and when the model is updated through the learning, stores the updated model.

If necessary, the model storage 231 stores the trained model by dividing the model into a plurality of versions depending on a training timing or a training progress.

The artificial neural network 231a illustrated in FIG. 6 is one example of artificial neural networks including a plurality of hidden layers but the artificial neural network of the present disclosure is not limited thereto.

The artificial neural network 231*a* may be implemented by hardware, software, or a combination of hardware and software. When a part or all of the artificial neural network 231*a* is implemented by the software, one or more commands which configure the artificial neural network 231*a* may be stored in the memory 230.

The database 232 stores input data obtained from the input interface 220, learning data (or training data) used to learn a model, a learning history of the model, and so forth.

The input data stored in the database 232 may be not only data which is processed to be suitable for the model learning but also input data itself which is not processed.

The learning processor 240 is a configuration corresponding to the learning processor 130 of FIG. 3.

The learning processor 240 may train (or learn) the artificial neural network 231*a* using training data or a training set.

The learning processor 240 may immediately obtain data which is obtained by pre-processing input data obtained by the processor 260 through the input interface 220 to learn the artificial neural network 231*a* or obtain the pre-processed input data stored in the database 232 to learn the artificial neural network 231*a*.

Specifically, the learning processor 240 repeatedly may train the artificial neural network 231*a* using various learning techniques described above to determine optimized model parameters of the artificial neural network 231*a*.

In this specification, the artificial neural network which is trained using training data to determine parameters may be referred to as a learning model or a trained model.

Here, the trained model may infer result values even while being installed in a learning device 200 of an artificial neural net and may be transferred to and installed in another device such as a terminal 100 by a transceiver 210.

Further, when the learning model is updated, the updated learning model may be transmitted to the other device such as the terminal 100 via the transceiver 210 to be loaded.

The power supply 250 is a configuration corresponding to the power supply 190 of FIG. 3.

A redundant description for corresponding configurations will be omitted.

Figure 7:
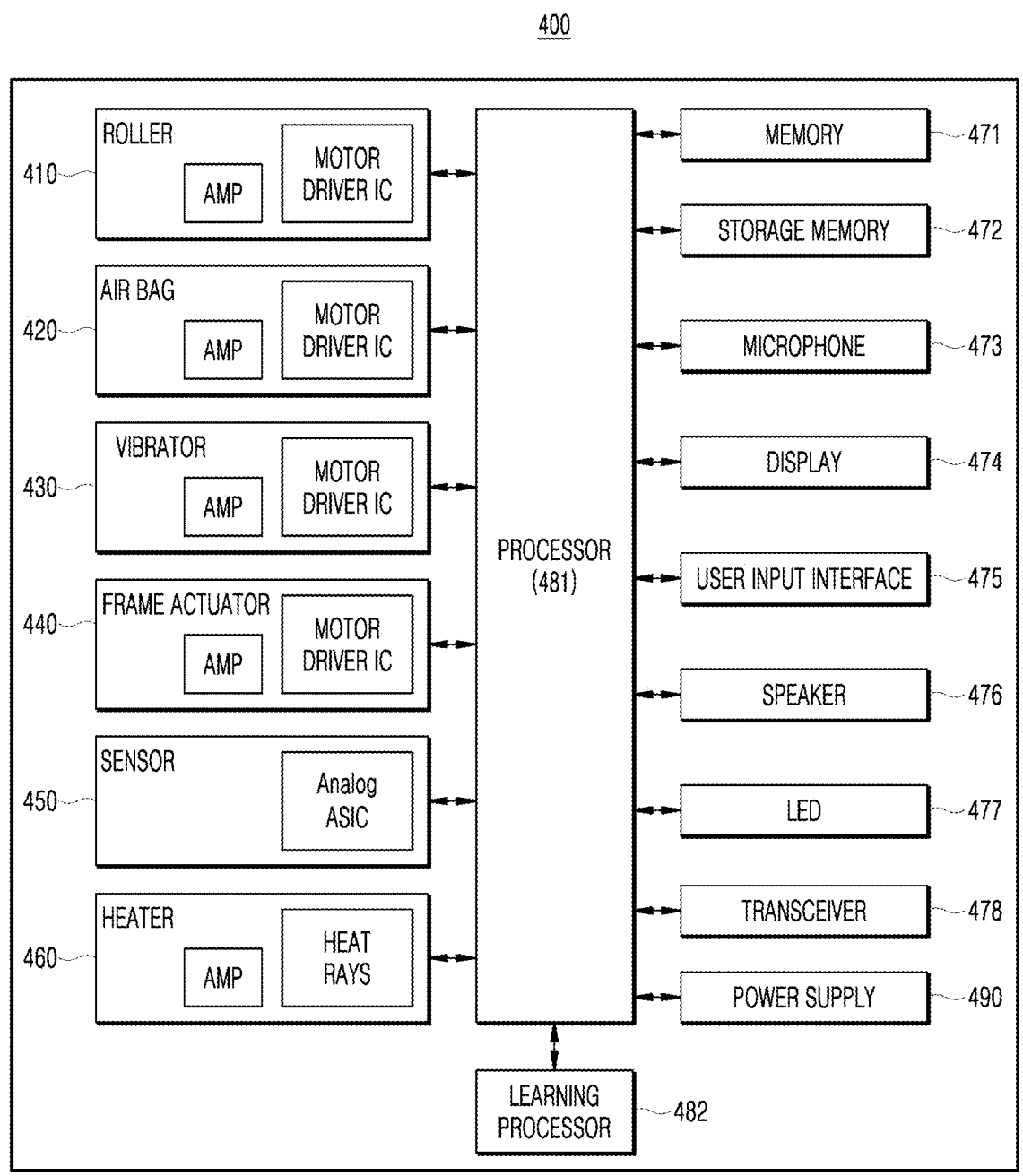
FIG. 7 is a block diagram of a massage chair according to an embodiment of the present disclosure.

FIG. 7 is a block diagram of a massage chair according to an embodiment of the present disclosure.

Referring to FIG. 7, components of a massage chair 400 according to an embodiment of the present disclosure are illustrated. The massage chair 400 may be configured to include driver systems 410 to 460 which perform action items, a processor 481 which controls the driver systems, a learning processor 482 used to train the artificial intelligence model, various electronic modules 471 to 478 to control the driver systems, and a power supply 490.

The driver system may be configured to include a roller 410, an air bag 420, a vibrator 430, a frame actuator 440, a sensor 450, and a heater 460. Among the components of the driver system, the roller 410, the air bag 420, the vibrator 430, and the frame actuator 440 may include amplifiers and motor driver ICs. The sensor 450 may be configured to include an analog ASIC which processes an analog signal, and the heater 460 may be configured to include heat rays.

The memory 471 loads data and various programs stored in the storage memory 472.

The storage memory 472 stores a program and data which perform various action items by controlling the driver system. Specifically, the storage memory 472 stores an artificial intelligence learning model, for example, a deep neural network which analyzes a video signal, an audio signal, and a subtitle, and extracts an action item based on the multimedia information. Further, the storage memory 472 stores a control protocol for communication with the controller 178 of the massage chair control apparatus 100.

The microphone 473 functions to collect voices of the user. The user voice data collected by the monitoring is converted into a feedback signal to be transmitted to the massage chair control apparatus 100, and the processor 180 corrects a control code which executes the action item, based on the feedback signal.

The display 474 functions to display an operating state of the massage chair 400.

The user input interface 475 may be implemented by a button or a touch input device, and issues an instruction to execute an action item of the massage chair 400.

The speaker 476 may output various sound effects while driving the massage chair 400.

The LED 477 displays ON/OFF of the power and various functions of the massage chair 400.

The transceiver 478 functions to receive a control code in accordance with the control protocol from the controller 178 of the massage chair control apparatus 100. The control code may be received through an infrared method or Internet, in other words, a wireless LAN such as WiFi, depending on the type of control protocol.

The power supply 490 may be configured to include a battery which supplies the power to the components of the massage chair 400 and an adaptor which converts an AC current into a DC current.

The massage chair control apparatus according to an embodiment of the present disclosure may be implemented as the terminal 100 or the set-top box 101. The terminal 100 and the set-top box 101 may be configured to include the processor 180 as a component.

The massage chair control apparatus 100 or the processor 180, which is an execution agent of a massage chair control method according to an embodiment of the present disclosure, 4-dimensionally may express a multimedia effect used at a timing of playing an input image by executing the action item of the massage chair, based on the multimedia effect according to analysis of an input image performed before playing an input image.

Figure 8:
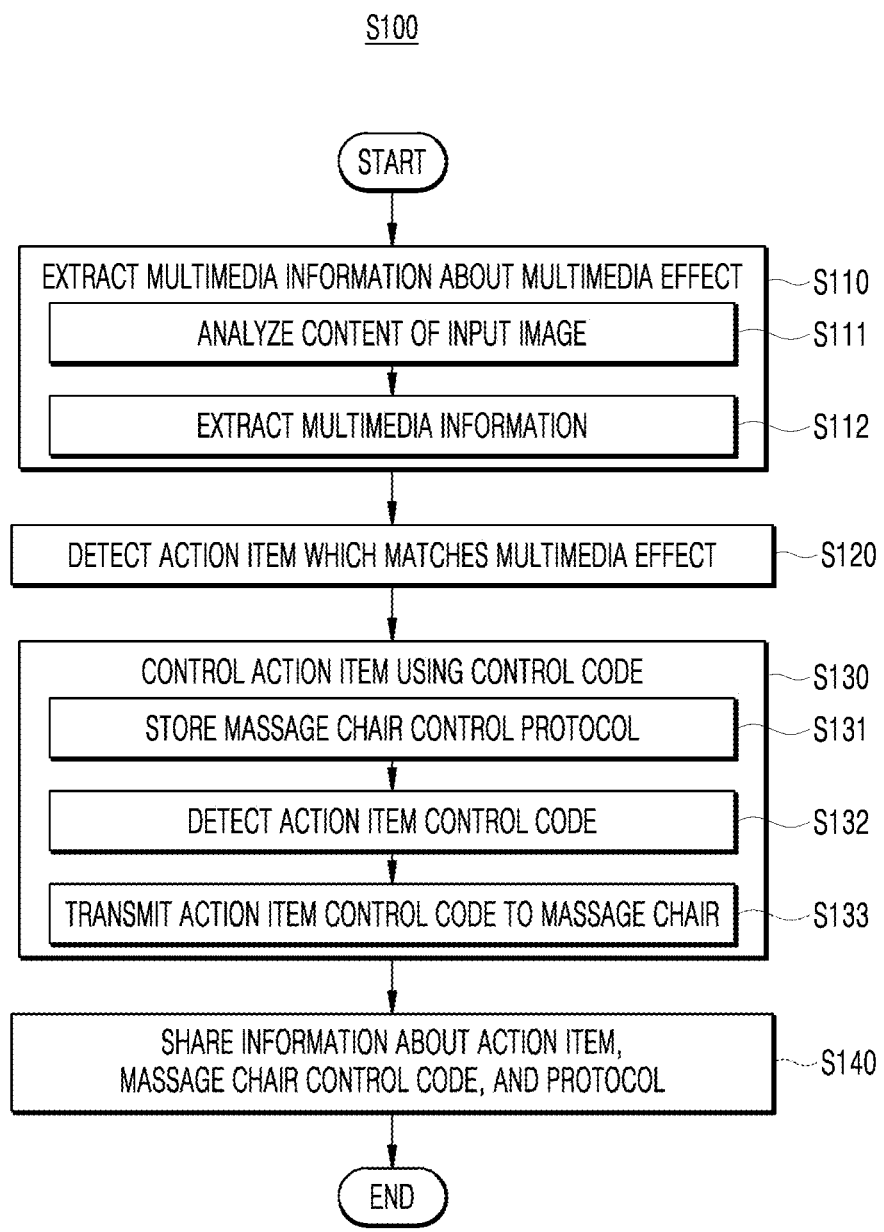
FIG. 8 is a flowchart of a massage chair control method according to an embodiment of the present disclosure.

FIG. 8 is a flowchart of a massage chair control method according to an embodiment of the present disclosure.

Referring to FIG. 8, the processor 180 may extract multimedia information about the multimedia effect used in the input image through content analysis of the input image (S110). Here, according to the content analysis, the multimedia effect used in the input image, that is, an image effect and a sound effect, are analyzed by using a feature extracted from a video, an audio, and a subtitle, which configure the input image.

The input image is stored in the data storage unit such as a server 300 and when the massage chair control apparatus which is implemented as the terminal 100 or the set-top box 101 requests the image, the stored image is provided to the massage chair control apparatus 100 through the network 500. The massage chair control apparatus 100 outputs the input image and controls the massage chair 400 based on the content analysis result.

The input image may be provided by a streaming method or a download method but is not limited to any specific method.

The processor 180 may analyze the content of the input image (S111). A streaming signal for a TV output or an image signal from an image file for output of the terminal 100 may be input to the massage chair control apparatus 100. The streaming signal and the image signal may include a video signal and an audio signal, and when the input image is content from a foreign movie, subtitles may be further included.

The processor 180 may analyze the contents of the input image for at least one of the video signal, the audio signal, or the subtitle of the input image. Further, the content analysis may include complex analysis of the video signal, the audio signal, and the subtitles. The content analysis process is a process of identifying the multimedia effect used in the input image using a feature extracted from the video signal, the audio signal, and the subtitles. Further, the multimedia information may be extracted as a result of identifying the multimedia effect. Emotions of characters appearing in the input image which is being played, the mood in the scene, and the scene development may be predicted based on the multimedia effect. Further, an action item of the massage chair which may match a multimedia effect used to create the emotion, the mood, and the situation may be detected.

The processor 180 may complete the content analysis of the input image before starting to play the input image, or analyze the contents of the input image in real time together with the playing of the input image. At the time of real-time analysis, the processor 180 may complete the analysis of the corresponding frame before playing the frame of the input image.

Further, the processor 180 may use at least one of a deep neural network for video signal analysis, a deep neural network for audio signal analysis, or an algorithm for natural language processing of the subtitle for the frame extracted from the input image. For content analysis, video signal analysis may be primarily used, whereas the audio signal and the subtitle analysis results may be secondarily used. Multimedia information about the emotions of the characters in the scene, the mood in the scene, and scene development due to the multimedia effect used for the input image may be extracted by the content analysis (S112).

The processor 180 may classify the category of the multimedia effect used for the input image by using a deep neural network, which is trained by the learning, based on the features of the video signal, the audio signal, and the subtitle of the input image. Further, the emotion of the characters in the scene, the mood in the scene, and the scene development may be predicted based on the category to which the multimedia effect belongs.

The processor 180 may detect the action item of the massage chair which may match the multimedia effect based on the multimedia information (S120). Here, the action item includes various operations of the massage chair which may be performed by the driver systems 410 to 460 among the components of the massage chair 400.

The multimedia information may include a multimedia effect used for the input image, for example, a visual effect, a sound effect, and time information when the effect is used. A process of detecting an action item of the massage chair which may match the multimedia effect based on the multimedia information is necessary. For example, a process of matching the action item of the massage chair and the multimedia effect is determining how to operate the massage chair to realistically express a mood of being frightened, and how to operate the massage chair to realistically express a car chase in a scene. In this process, a matching table, which is determined in advance from being designed by people and is created by the correspondence of the multimedia effect and the action item, may be used.

Further, the deep neural network, which is trained by the learning, may perform the process of matching the multimedia effect and the action item. The training process for matching may be configured to include the learning of a body part for executing the action item, a type of the action item, a strength of the action item, and a duration of the action item.

The process of detecting the action item may include a process of matching a pre-created action item suitable for the multimedia effect and a process of creating a new action item suitable for the multimedia effect.

During the process of matching the multimedia effect and the action item, information on details of the action item may be used. The action item of the massage chair may be configured to include at least one of, or a combination of, kneading, knocking, pressing, vibrating, rolling, rubbing, stretching, finger-pressure, zero-gravity reclining, or heating performed on a body part of a human using the components 410 to 460 of the massage chair. Action items deemed suitable for expressing the emotions of the characters in the scene, the mood in the scene, and the scene development derived from the multimedia effect may be determined by the process of matching the deep neural network trained by the learning. Here, joy, anger, sorrow, pleasure, tension, and relief are examples of emotions; fear, urgency, and mood change are examples of moods in a scene; and doing an action, being in space, being underwater, and flying are examples of special situations that may be expressed by the action item of the massage chair 400 in a 4D environment.

Figure 9:
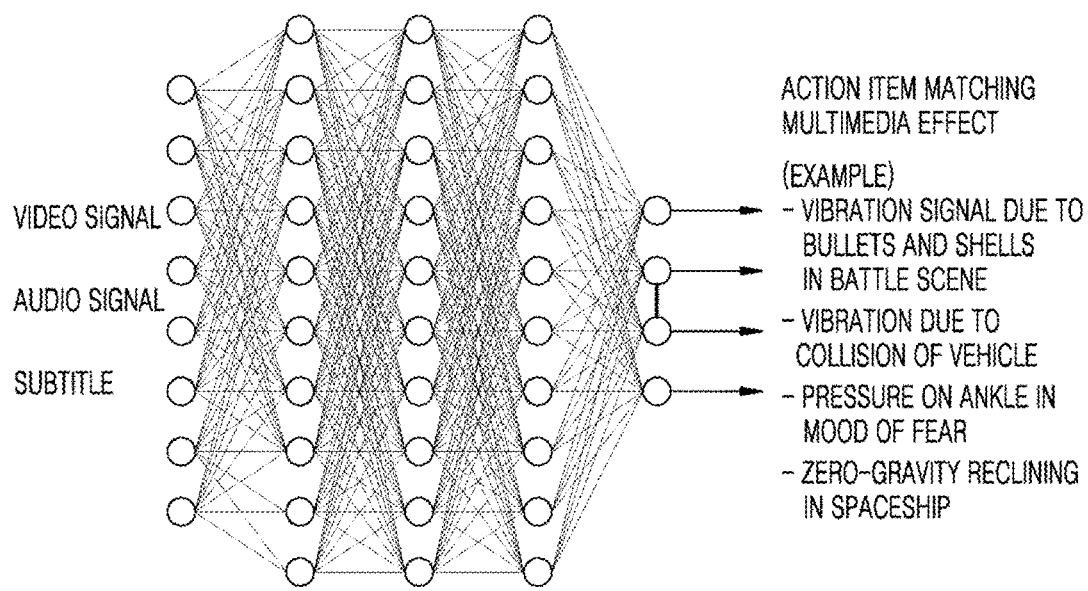
FIG. 9 is an exemplary diagram of a deep neural network according to an embodiment of the present disclosure.

FIG. 9 is an exemplary diagram of a deep neural network according to an embodiment of the present disclosure.

Referring to FIG. 9, an exemplary model of the deep neural network for extracting multimedia information about the multimedia effect and detecting the action item is illustrated. A data set used to train the deep neural network uses a video signal, an audio signal, and a subtitle as input data and outputs information about the action item as output data.

The process of detecting the action item from the input image, that is, the process of extracting the multimedia information and extracting the action item, may be performed by a plurality of deep neural networks or a plurality of layers in one neural network.

As illustrated in the example, other components may be combined with the vibrator serving as a main component to express vibrations caused by bullets and shells in a battle scene. Components such as the roller 410 and the air bag 420 may be combined to express vibrations caused by a car collision. Further, a zero-gravity state of a spaceship may be realized through zero-gravity posture control by using the frame actuator 440 of the massage chair.

The frame which configures the massage chair 400 may be changed at a plurality of angles by the frame actuator 440. A situation in which the characters in the input image are placed in a special situation, for example, a gravity zero state in a spaceship, may be implemented using the massage chair 400, which is a 4D device, by synchronizing a backrest, a seat, and a leg rest of the massage chair 400.

Figure 10:
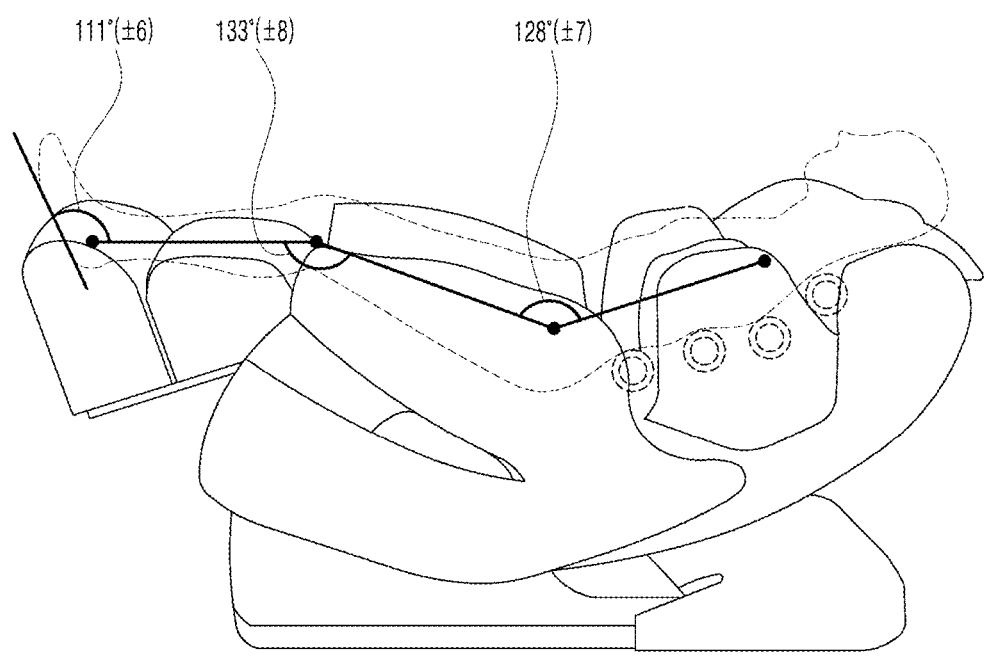
FIG. 10 is an exemplary diagram of zero-gravity reclining according to an embodiment of the present disclosure.

FIG. 10 is an exemplary diagram of a zero-gravity posture which may be implemented by a massage chair control method according to an embodiment of the present disclosure.

Referring to FIG. 10, according to a zero-gravity theory by NASA, in a posture in which the position of the foot is higher than or equal to the position of the head, when an angle) (110°) of an ankle, an angle (133°) of a knee, and an angle (128°) of a waist are maintained to within a tolerable error as illustrated in FIG. 10, a state similar to the zero-gravity state may be implemented.

A process of extracting multimedia information from the input image described till now and detecting the action item based on the multimedia information will be described with an example.

Figure 11:
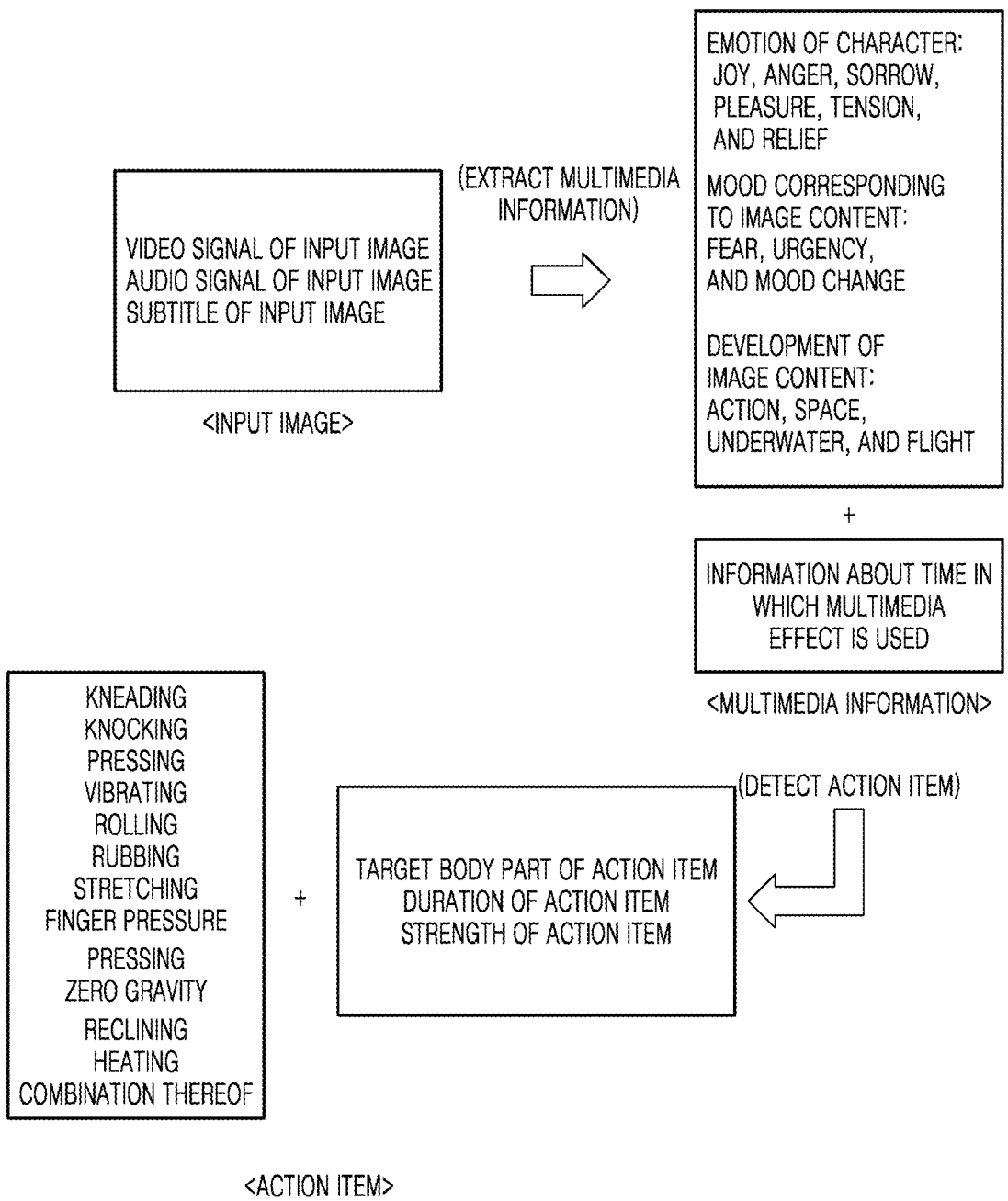
FIG. 11 is an exemplary diagram of extracting of multimedia information and detecting of an action item according to an embodiment of the present disclosure.

FIG. 11 is an exemplary diagram of extracting multimedia information and detecting an action item according to an embodiment of the present disclosure.

Referring to FIG. 11, the multimedia information may be extracted from the input image, that is, the video signal, the audio signal, and the subtitle included in the input image. The multimedia information includes information about the multimedia effect and time information in which the multimedia effect is used. The emotion of the character, the mood corresponding to the image content, and the development of the image content may be predicted by the multimedia effect. Further, the action item of the massage chair may be detected based on the multimedia information. The action item may be created in various types in accordance with various operations by the driver system of the massage chair, a target body part of the action item, a duration of the action item, and the strength of the action item.

The extraction of the multimedia information according to the embodiment of the present disclosure may be related to video storytelling. According to basic video storytelling, a psychological state of a main character in a story may be expressed by using a text-based story emotional curve, that is, using a horizontal axis of time and a vertical axis of a state of emotion. Further, an emotional curve of the image based on an image story learning method has been introduced. The emotional curve of the image has a disadvantage in that only the visual aspect in analyzing the video contents is considered.

The multimedia information according to the embodiment of the present disclosure is based on the video storytelling. However, the multimedia information is not only based on the video which represents a visual effect for predicting the psychological state of the main character, the mood in the scene, and the scene development, but also additionally uses a sound and a subtitle, that is, a text.

The processor 180 may control the action item of the massage chair by using a control code of the action item (S130).

The control of the action item (S130) may be configured to include storing of a massage chair control protocol (S131), detecting of an action item control code (S132), and transmitting of the action item control code to the massage chair (S133).

The controller 178 of the massage chair control apparatus 100 corresponding to the terminal 100 or the set-top box 101 is operated by a remote controller to control the action item of the massage chair 400. The massage chair 400 may be controlled by an infrared method or a network 500, for example, a wireless LAN such as WiFi or a short-range communication method such as a Bluetooth, depending on the method of the remote controller.

The massage chair 400, which receives the control code of the action item from the massage chair control apparatus, may store information about the action item already configured in accordance with the type of the operation mode and a control code corresponding thereto in advance. Further, the massage chair 400 may execute a new action item by receiving a control code set which is newly created from a combination of the control code which operates the driver system of the massage chair 400.

Based on the feedback signal transmitted from the massage chair 400, the massage chair control apparatus 100 may transmit a control code corrected from an original control code which executes the action item to the massage chair 400, thus controlling the action item by reflecting the feedback information from the user. The feedback signal regards the reaction of the user, for example.

The processor 180 detects the control code of the action item from the stored control protocol (S220), and the controller 178 controls the transmission of the control code to the massage chair (S230). The massage chair 400 receives the control code and controls the action item using the control code.

The action item corresponding to the original control code is executed, and the massage chair 400 collects voice data of the user by using user monitoring, for example, the microphone, and transmits the collected voice data to the massage chair control apparatus 100 (S250). The satisfaction and additional order of the user regarding the action item executed by the voice recognition and analysis process based on the voice data of the user who uses the servers 300 may be interpreted. For example, when an exclamation which represents the satisfaction of the user is analyzed as a feedback signal for the executed action item, the processor 180 may modify the corresponding control code to extend an execution time of the action item or increase the strength of the action item. In contrast, when a sound of a user groaning is analyzed as a feedback signal, the processor 180 may modify the corresponding control code to shorten the execution time of the action item or reduce the strength of the action item.

Figure 12:
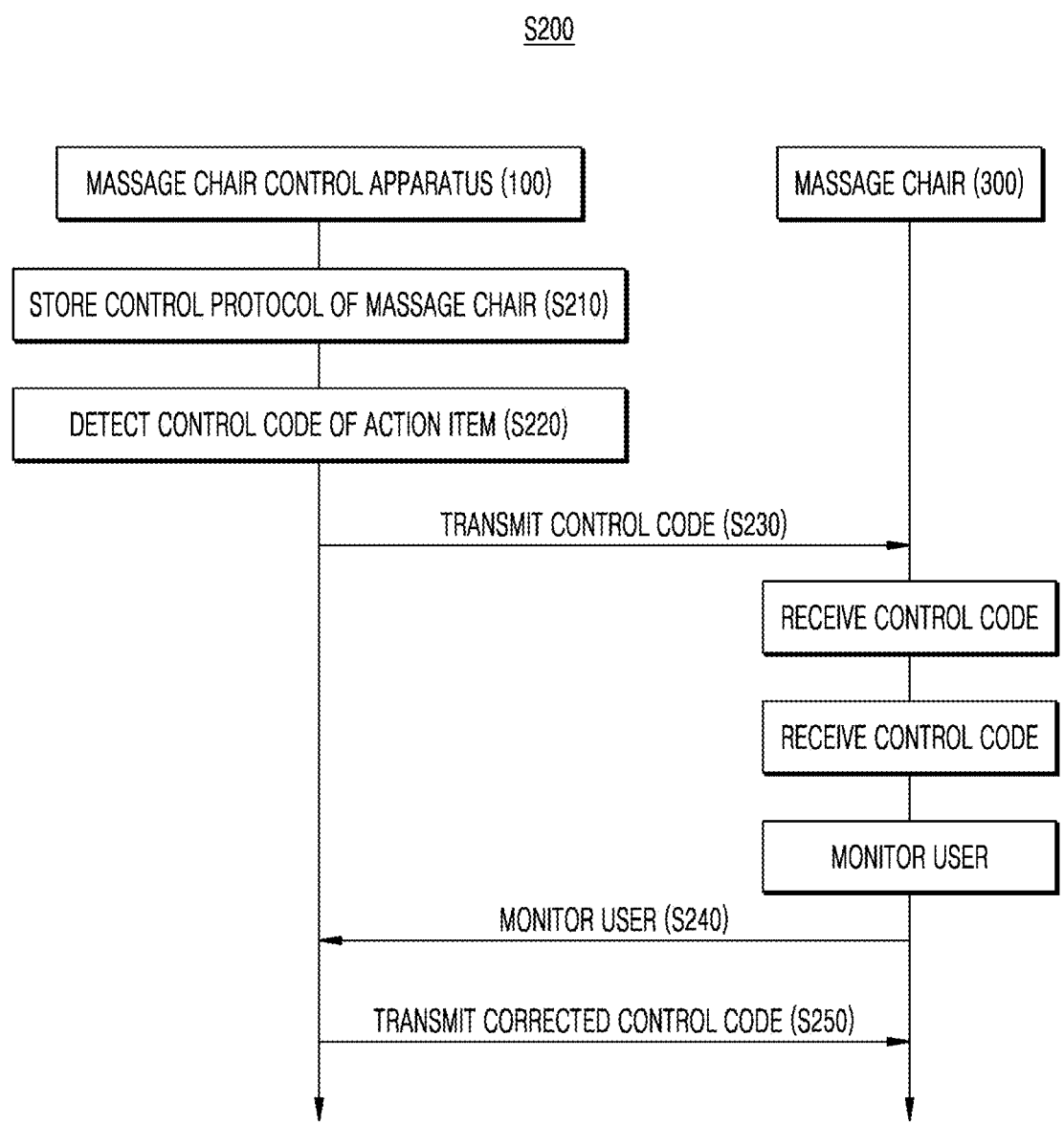
FIG. 12 is a flowchart of data between a massage chair control apparatus according to an embodiment of the present disclosure and a massage chair.

FIG. 12 is a flowchart of data between a massage chair control apparatus according to an embodiment of the present disclosure and a massage chair.

Referring to FIG. 12, the action item control (S130) performed by the massage chair control apparatus 100 may be configured to include storing of a massage chair control protocol (S131), detecting of an action item control code (S132), and transmitting of the action item control code to the massage chair (S133). The processor 180 may adjust the controller to synchronize timings of the multimedia effect and the action item based on the feedback signal for the control code received from the massage chair and the time information included in the multimedia information.

Figure 13:
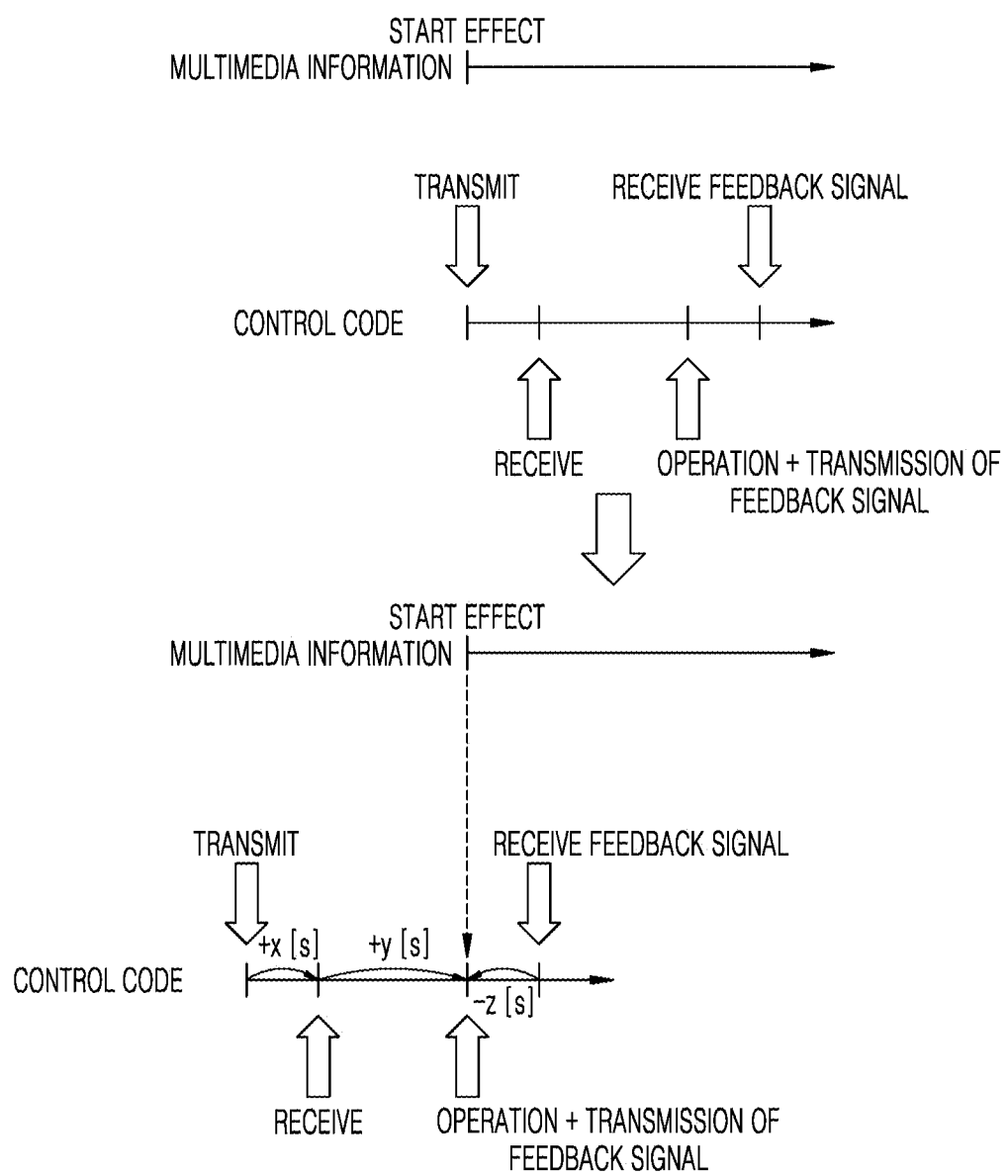
FIG. 13 is an exemplary diagram of synchronization between multimedia information and an action item according to an embodiment of the present disclosure.

FIG. 13 is an exemplary diagram of synchronization between multimedia information and an action item according to an embodiment of the present disclosure.

Referring to FIG. 13, a state in which timings of the multimedia effect and the action item are not synchronized and a state in which the timings are synchronized are illustrated at the top and bottom, respectively. Referring to the top, when the multimedia effect starts, the massage chair control apparatus 100 transmits the control code to the massage chair 400. When a time of +x(s) elapses from the timing of transmitting the control code, the massage chair 400 receives the control code, and when a time of +y(s) elapses, executes the action item by using the control code, and transmits the feedback signal to the massage chair control apparatus 100. The massage chair control apparatus 100 receives the feedback signal when a time of +z(s) elapses from the timing of executing the action item. In this case, there may be a timing difference of x+y(s) between the timing of transmitting the control code and the timing of executing the action item. In order to synchronize the multimedia effect and the action item, it is necessary to match the timing of executing the action item and the timing of transmitting the control code. After reading the multimedia information, the processor 180 controls the controller to transmit the control code to the massage chair at a timing x+y(s) ahead of the timing of starting the multimedia effect to synchronize the timings of the multimedia effect and the action item.

The massage chair control apparatus 100 according to the embodiment of the present disclosure may share the information about the action item, information about the massage chair control code, and the control protocol (S140).

Specifically, the massage chair control apparatus 100 may further include a wireless or wired transceiver which shares information with another user by directly or indirectly transmitting, through a server, at least one of information about the action item which matches the multimedia information, information about the control code which matches the action item, or the control protocol of the massage chair.

As described above, according to the embodiment of the present disclosure, it is possible to classify multimedia effects used in an input image, extract multimedia information, and extract action items, using a deep neural network model.

Further, it is possible to synchronize the timing of a multimedia effect and the timing of a corresponding action item through a feedback signal from the massage chair.

Further, it is possible to control the action item of the massage chair which is linked with the multimedia effect of the input image.

Embodiments according to the present disclosure described above may be implemented in the form of computer programs that may be executed through various components on a computer, and such computer programs may be recorded in a computer-readable medium. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

The singular forms "a," "an" and "the" in this present disclosure, in particular, claims, may be intended to include the plural forms as well. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

Operations constituting the method of the present disclosure may be performed in appropriate order unless explicitly described in terms of order or described to the contrary. The present disclosure is not necessarily limited to the order of operations given in the description. All examples described herein or the terms indicative thereof ("for example," etc.) used herein are merely to describe the present disclosure in greater detail. Therefore, it should be understood that the scope of the present disclosure is not limited to the exemplary embodiments described above or by the use of such terms unless limited by the appended claims. Also, it should be apparent to those skilled in the art that various modifications, combinations, and alternations can be made depending on design conditions and factors within the scope of the appended claims or equivalents thereof.

Therefore, technical ideas of the present disclosure are not limited to the above-mentioned embodiments, and it is intended that not only the appended claims, but also all changes equivalent to claims, should be considered to fall within the scope of the present disclosure.

What is claimed is:

1. A massage chair control method configured to be performed by a massage chair control apparatus, the massage chair control method comprising:
    extracting multimedia information corresponding to a multimedia effect used in an input image through content analysis of the input image;
    based on the multimedia information, detecting an action item of a massage chair; and
    controlling the action item of the massage chair by using a control code of the action item,
    wherein extracting the multimedia information comprises:
        recognizing an object in the input image through video signal analysis based on deep learning-based convolutional neural network (CNN), and
        extracting the multimedia information corresponding to the multimedia effect based on the recognized object, and
    wherein controlling the action item comprises:
        executing the action item corresponding to the control code,
        based on executing the action item corresponding to the control code, receiving a feedback signal for the control code transmitted from the massage chair, and
        modifying the control code to control an execution time of the action item or a strength of the action item based on the feedback signal.

2. The massage chair control method according to claim 1, wherein the content analysis of the input image is performed on at least one of a video signal, an audio signal, or a subtitle of the input image, and comprises analysis of a frame of the input image before playing the input image at a time of real-time analysis of the input image.

3. The massage chair control method according to claim 1, wherein the content analysis of the input image is performed on a frame extracted from the input image by using at least one of a deep neural network for video signal analysis, a deep neural network for audio signal analysis, or an algorithm for natural language processing of a subtitle.

4. The massage chair control method according to claim 1, wherein the content analysis of the input image comprises classification of the multimedia effect used in the input image, through video signal analysis, audio signal analysis, and natural language processing of a subtitle of the input image.

5. The massage chair control method according to claim 1, wherein extracting the multimedia information comprises:
    extracting the multimedia information based on the multimedia effect used in the input image; and
    extracting information about a time in which the multimedia effect is used.

6. The massage chair control method according to claim 1, wherein detecting the action item comprises:
    matching the multimedia effect classified by a clustering model of a deep neural network and an action item of the massage chair that expresses or implements the multimedia effect.

7. The massage chair control method according to claim 6, wherein detecting the action item comprises:
    matching an action item corresponding to at least one of, or a combination of, kneading, knocking, pressing, vibrating, rolling, rubbing, stretching, finger-pressure, zero-gravity reclining, or heating, as the action item of the massage chair that matches the multimedia effect used for: an emotion including joy, anger, sorrow, pleasure, tension, and relief; a mood including fear, urgency, and mood change; and a situation including doing an action, being in space, being underwater, and flying.

8. The massage chair control method according to claim 1, wherein controlling the action item comprises:
storing a control protocol of the massage chair;
detecting the control code of the action item from the control protocol; and
transmitting the control code to the massage chair.

9. The massage chair control method according to claim 1, wherein controlling the action item comprises:
synchronizing a timing of the action item, based on a feedback signal and time information included in the multimedia information.

10. The massage chair control method according to claim 1, further comprising:
sharing information with another user by directly or indirectly transmitting, through a server, at least one of information about the action item that matches the multimedia information, information about the control code of the massage chair that matches the action item, or a control protocol of the massage chair.

11. A massage chair control apparatus, comprising:
a processor configured to, based on extracting multimedia information corresponding to a multimedia effect used in an input image through content analysis of the input image, detect an action item of a massage chair; and
a controller configured to control the action item by using a control code of the action item,
wherein the processor is configured to extract the multimedia information by:
recognizing an object in the input image through video signal analysis based on deep learning-based convolutional neural network (CNN), and
extracting the multimedia information corresponding to the multimedia effect based on the recognized object, and
wherein the controller is configured to:
execute the action item corresponding to the control code,
based on executing the action item corresponding to the control code, receive a feedback signal for the control code transmitted from the massage chair, and
modify the control code to control an execution time of the action item or a strength of the action item based on the feedback signal.

12. The massage chair control apparatus according to claim 11, wherein the processor is configured to analyze contents of the input image with respect to at least one of a video signal, an audio signal, or a subtitle of the input image, and analyze a frame of the input image before playing the input image at a time of real-time analysis of the input image.

13. The massage chair control apparatus according to claim 11, wherein the processor is configured to analyze contents of the input image by using at least one of a deep neural network for video signal analysis, a deep neural network for audio signal analysis, or an algorithm for natural language processing of a subtitle, for a frame extracted from the input image.

14. The massage chair control apparatus according to claim 11, wherein the processor is configured to classify the multimedia effect used in the input image using a deep neural network trained by learning, based on features of a video signal, an audio signal, and a subtitle of the input image.

15. The massage chair control apparatus according to claim 11, wherein the processor is configured to extract the multimedia information corresponding to the multimedia effect used in the input image, and information about a time in which the multimedia effect is used.

16. The massage chair control apparatus according to claim 11, wherein the processor is configured to match the multimedia effect classified by a clustering model of a deep neural network and an action item of the massage chair that expresses the multimedia effect.

17. The massage chair control apparatus according to claim 16, wherein the processor is configured to match an action item corresponding to at least one of, or a combination of, kneading, knocking, pressing, vibrating, rolling, rubbing, stretching, finger-pressure, zero-gravity reclining, or heating, as the action item of the massage chair that matches the multimedia effect used for: an emotion including joy, anger, sorrow, pleasure, tension, and relief; a mood including fear, urgency, and mood change; and a special situation including doing an action, being in space, being underwater, and flying.

18. The massage chair control apparatus according to claim 11, wherein:
the processor is configured to detect the control code of the action item from a stored control protocol, and
the controller is configured to control transmission of the control code to the massage chair.

19. The massage chair control apparatus according to claim 11, wherein the processor is configured to adjust the controller to synchronize timings of the multimedia effect and the action item, based on a feedback signal for the control code received from the massage chair and time information included in the multimedia information.

20. The massage chair control apparatus according to claim 11, further comprising:
a transceiver configured to share information with another user by directly or indirectly transmitting, through a server, at least one of information about the action item that matches the multimedia information, information about the control code that matches the action item, or a control protocol of the massage chair.

* * * * *